(12) United States Patent
Zhao et al.

(10) Patent No.: US 9,263,226 B2
(45) Date of Patent: Feb. 16, 2016

(54) RADIATION DEVICE INSTALLATION HOUSING AND X-RAY GENERATOR

(71) Applicant: Nuctech Company Limited, Beijing (CN)

(72) Inventors: Ziran Zhao, Beijing (CN); Zhiqiang Chen, Beijing (CN); Xilei Luo, Beijing (CN); Fuhua Ding, Beijing (CN); Wanlong Wu, Beijing (CN); Zhimin Zheng, Beijing (CN)

(73) Assignee: Nuctech Company Limited (CN)

( * ) Notice: Subject to any disclaimer, the term of this patent is extended or adjusted under 35 U.S.C. 154(b) by 233 days.

(21) Appl. No.: 14/005,605

(22) PCT Filed: Dec. 31, 2012

(86) PCT No.: PCT/CN2012/088082
§ 371 (c)(1),
(2) Date: Sep. 17, 2013

(87) PCT Pub. No.: WO2013/102426
PCT Pub. Date: Jul. 11, 2013

(65) Prior Publication Data
US 2014/0050305 A1 Feb. 20, 2014

(30) Foreign Application Priority Data

Jan. 6, 2012 (CN) .......................... 2012 1 0003659

(51) Int. Cl.
*H01J 35/16* (2006.01)
*H01J 35/10* (2006.01)
(Continued)

(52) U.S. Cl.
CPC ................ *H01J 35/16* (2013.01); *G01N 23/04* (2013.01); *H01J 35/105* (2013.01); *H01J 35/106* (2013.01);
(Continued)

(58) Field of Classification Search
CPC ............ H01J 35/16; H01J 35/18; H05G 1/08; H05G 1/085
USPC .......................................... 378/121, 141, 200
See application file for complete search history.

(56) References Cited

U.S. PATENT DOCUMENTS

| 4,646,338 | A | | 2/1987 | Skillicorn | |
|-----------|---|---|--------|-----------|---|
| 5,222,118 | A | * | 6/1993 | Gerth ...................... | H05G 1/04 378/199 |

(Continued)

FOREIGN PATENT DOCUMENTS

| CN | 1711007 A | 12/2005 |
|----|-----------|---------|
| CN | 1994027 A | 7/2007 |

(Continued)

OTHER PUBLICATIONS

"International Application Serial No. PCT/CN2012/088082, International Search Report mailed Apr. 11, 2013", (w/ English Translation), 8 pgs.

(Continued)

*Primary Examiner* — Allen C. Ho
(74) *Attorney, Agent, or Firm* — Schwegman Lundberg & Woessner, P.A.

(57) ABSTRACT

Embodiments include an X-ray generator including a radiation device installation housing and an X-ray generator. In various embodiments, the radiation device installation housing comprises a housing body, a flange fixedly provided on an inner wall of the housing body and shaped in circular and a compensation device fixedly or movably connected with the flange in a liquid tight manner; a liquid receiving cavity for receiving an insulating liquid formed between one side of two opposite sides of the compensation device and the inner wall of the housing body as well as the flange; a compensation device moving space formed between another side of the two opposite sides of the compensation device opposed to the inner wall of the housing body and an inner wall of the flange.

10 Claims, 9 Drawing Sheets

(51) Int. Cl.
*H01J 35/12* (2006.01)
*H05G 1/08* (2006.01)
*G01N 23/04* (2006.01)
*H05G 1/02* (2006.01)
*H05G 1/04* (2006.01)

(52) U.S. Cl.
CPC ................ *H01J 35/12* (2013.01); *H05G 1/025* (2013.01); *H05G 1/04* (2013.01); *H05G 1/08* (2013.01); *H05G 1/085* (2013.01)

(56) References Cited

U.S. PATENT DOCUMENTS

| | | | |
|---|---|---|---|
| 5,285,492 A * | 2/1994 | Janouin | H05G 1/04 378/141 |
| 5,384,821 A | 1/1995 | Jedlitschka et al. | |
| 6,074,092 A * | 6/2000 | Andrews | F04D 13/16 378/141 |
| 6,366,642 B1 * | 4/2002 | Andrews | H01J 35/105 378/117 |
| 6,563,908 B1 | 5/2003 | Enck, Jr. | |
| 7,221,736 B2 * | 5/2007 | Heidrich | H05G 1/02 165/104.32 |
| 7,236,570 B2 * | 6/2007 | Canfield | H05G 1/04 378/141 |
| 7,302,042 B2 * | 11/2007 | Hansen et al. | 378/141 |
| 7,376,218 B2 * | 5/2008 | Chapin | H05G 1/04 378/119 |
| 2006/0067478 A1 | 3/2006 | Canfield | |
| 2006/0171505 A1 | 8/2006 | Heidrich et al. | |
| 2008/0043919 A1 | 2/2008 | Chapin et al. | |

FOREIGN PATENT DOCUMENTS

| | | |
|---|---|---|
| CN | 101128081 A | 2/2008 |
| CN | 102595753 A | 7/2012 |
| JP | 5871999 U | 5/1983 |
| JP | 06-111991 A | 4/1994 |
| JP | 09027394 A | 1/1997 |
| JP | 2001307668 A | 11/2001 |
| JP | 2003-123999 A | 4/2003 |
| JP | 2010067544 A | 3/2010 |
| WO | WO-2013/102426 A1 | 7/2013 |

OTHER PUBLICATIONS

"International Application Serial No. PCT/CN2012/088082, Written Opinion mailed Apr. 11, 2013", 5 pgs.

"European Application Serial No. 12864584.3, Extended European Search Report mailed Jun. 1, 2015", 9 pgs.

"International Application Serial No. PCT/CN2012/088082, International Preliminary Report on Patentability mailed Apr. 11, 2013", W/ English Translation, 15 pgs.

* cited by examiner

RADIATION DEVICE INSTALLATION HOUSING AND X-RAY GENERATOR

This application claims and enjoys the benefit and priority from Chinese Patent Application No. 201210003659.3, filed on Jan. 6, 2012, the disclosure of which is incorporated herein in its entirety by reference.

FIELD OF THE INVENTION

The present application relates to the X-ray generator field, more particularly, to a radiation device installation housing and an X-ray generator provided with the radiation device installation housing.

DESCRIPTION OF THE RELATED ART

The X-ray source and the image collecting and processing system are kernel parts of the security inspection apparatus using the X-ray imaging technique. Since the imaging quality and the inspection effect of the security inspection apparatus are largely depended on the performance of the X-ray source, the quality and performance of the X-ray source is critical to the security inspection apparatus. Presently, the X-ray source of the security inspection apparatus using the X-ray imaging technique mainly employs the X-ray generator.

The typical X-ray generator includes an X-ray tube assembly, a high frequency and high voltage generator, a filament power supply module, a cooling system and a housing. The X-ray tube assembly includes an X-ray tube and a collimator (or a pre-collimator) fixedly connected with an anode and a cathode sheath of the X-ray tube. The X-ray tube assembly is disposed within the housing. The housing is made of sheet material and is formed by welding and screw connection. The collimator and the housing are two individual components or parts which are fixedly connected together. A beam exiting aperture is provided on the collimator and a beam exiting opening is provided on the housing. Generally, the inner wall of the housing except for the beam exiting opening is provided with X-ray protection layer to shield the X-ray in the non-main beam direction. The high frequency and high voltage generator is electrically connected with the anode and cathode of the X-ray tube, and the high frequency and high voltage generator is used to supply DC voltage to the anode and the cathode of the X-ray tube. The filament power supply module is electrically connected with the cathode of the X-ray tube, and is used for supplying the high frequency pulse voltage to the cathode of the X-ray tube. When the filament power supply module supplies the high frequency pulse voltage to the cathode of the X-ray tube, the cathode of the X-ray tube would emit an electron flow to impact the anode of the X-ray tube under the action of the high voltage electric field, so as to stimulate the X-ray beam which can in turn pass through the beam exiting aperture and the beam exiting opening to emit the housing. The cooling system is used to dissipate the heat accumulated on the X-ray tube for avoiding burnout of the X-ray tube. The housing and the collimator constitute an enclosed space in which the cooling liquid is filled, which is an important component in the cooling system.

The above conventional technique in the prior arts at least has following problems:

Since the X-ray tube in the housing will generate a large amount of the heat during the working process, the insulating liquid is heated and expanded (that is called as "thermal expansion"). The heated and expanded insulating liquid will apply a larger pressure to the electronic elements within the housing and press the inner wall of the housing to deform the housing outwardly. When the X-ray tube is shut down after its work, the insulating liquid will be cooled and contracted (that is called as "cold contraction"). After the insulating liquid is cooled and contracted, the atmosphere outside the housing will press the outer wall of the housing to deform the housing inwardly. The expansion and contraction of the volume of the insulating liquid will cause the pressure to which the electronic elements subjected to vary in a wide range, so that the housing and the electronic elements within the housing are easily damaged due to change of the pressure from the insulating liquid.

SUMMARY OF THE INVENTION

The present invention has been made to overcome or alleviate at least one aspects of the above problems or disadvantages in the prior arts.

An object of the present invention is to provide a radiation device installation housing and an X-ray generator provided with the radiation device installation housing.

In order to achieve an aspect of above objects, the present invention provides following technical solution:

The radiation device installation housing includes a housing body, and further comprises a flange fixedly provided on an inner wall of the housing body and having a circular shape and a compensation device fixedly or movably connected with the flange in a liquid tight manner.

A liquid receiving cavity for receiving an insulating liquid is formed between one side of two opposite sides of said compensation device and said inner wall of the housing body as well as said flange.

A compensation device moving space for allowing said compensation device to deform or move toward a direction away from or close to said insulating liquid is formed between another side of said two opposite sides of said compensation device opposed to said inner wall of the housing body and an inner wall of the flange.

The technical solution of the present invention can have the following technical effects:

Since the flange having circular shape is fixedly provided on the inner wall of the housing body of the present invention, the compensation device fixedly or moveably connected with the flange in the liquid tight manner is provided on the flange, during the insulating liquid filled in the housing body occurs thermal expansion and contraction, the compensation device (for example, preferably the elastic drum membrane or the piston) can be deformed or moved within the compensation device moving space.

When the insulating liquid is thermally expanded, the expanded insulating liquid can press the compensation device to allow it to be deformed or moved toward the direction away from the insulating liquid, that is, the direction close to the inner wall of the housing body, the deformed or moved compensation device compresses the volume of the compensation device moving space and increases the volume of the liquid receiving cavity, the increased liquid receiving cavity reduces the pressure applied to the housing body and the electric components within the housing body from part expanded insulating liquid.

When the insulating liquid is thermally contracted, the volume of the insulating liquid is contracted, and the intensity of pressure within the housing body is smaller than the atmospheric pressure outside the housing body. The atmosphere compresses the compensation device to allow it to be deformed toward the direction close to the insulating liquid and press the insulating liquid, so that the insulating liquid is ensured to be filled everywhere within the housing body, and the pressure, which the electrical components within the housing body have been undergone, from the insulating liquid is substantially constant. The pressure will be not too large, so that the housing body and the electrical components within the housing body will not be crushed, thus, the technical problem of the housing body and the electrical components within the housing body in the prior art might be damaged due to the pressure from the insulating liquid can be solved.

At the same time, when the oil is injected into the housing body in the vacuum oil injection manner, after finishing injection of the insulating liquid into the housing body, the compensation device will press the insulating liquid by means of elastically deformation or moving, which ensures the insulating liquid being filled all over the housing body and then, ensures the oil amount within the housing body to meet the requirements.

The preferable technical solutions of the present invention are provided as following:

Preferably, the compensation device is an elastic drum membrane which is able to fixedly connect with a port of the flange away from the inner wall of the housing body and cover on the port of the flange away from the inner wall of the housing body, the elastic drum membrane is able to deform within the compensation device moving space toward the direction away from or close to the insulating liquid; or, the compensation device is a piston embedded in the flange, the piston is able to move within the compensation device moving space toward the direction away from or close to the insulating liquid, an escape protection structure used to prevent the piston from escaping from the flange is further provided between the piston and the inner wall of the flange.

Preferably, an outer profile of the cross section of the flange has a shape of circular, elliptic, triangular, rectangular or polygonal in addition to the triangular and the rectangular.

And/or, air guiding holes respectively in communication with the external air and the compensation device moving space are opened on the housing body.

And/or, materials for producing the elastic drum membrane is nitrile-butadiene rubber or fluorine rubber; and/or, the elastic drum membrane is fixedly on the flange through fasteners, or one side of the elastic drum membrane away from the inner wall of the housing body is provided with a pressing plate, an edge of the elastic drum membrane is pressed against onto the flange by an edge of the pressing plate, and the edge of the pressing plate is fixedly connected with the flange through fasteners, a central region of the pressing plate is opened with one or two or more through holes through which the insulating liquid is freely passed.

And/or, a central region of one side of the elastic drum membrane close to the pressing plate is formed in corrugation.

And/or, the pressing plate is formed in a disk shape, and the fasteners are equiangularly distributed on the pressing plate, the elastic drum membrane and the flange in a circumferential direction of the pressing plate.

And/or, the housing comprises a housing main body, a first housing cover and a second housing cover, wherein:

The first housing cover and the second housing cover are respectively fixedly provided on two opposite ports of the housing main body, and the flange is fixedly provided on the second housing cover or the first housing cover.

The housing main body has an integrated structure, and the material for producing the first housing cover and the second housing cover is the same as the material of the housing main body.

Preferably, at least one projections having external protruding shape are fixedly provided at one side of the elastic drum membrane close to the flange or the pressing plate, a recess having concave shape is opened on the flange or the pressing plate, the projections are embedded in the recess.

And/or, the housing main body is made in aluminum or aluminum-alloy material by employing stretching process or cutting process.

And/or, the flange is integrated with the second housing cover.

And/or, at least one reinforced ribs integrated with the housing main body are disposed on an outer surface of the housing main body, and screw holes are provided on the reinforced ribs.

And/or, a sealing strip is further provided between the first housing cover and the housing main body and/or between the second housing cover and the housing main body, wherein:

A stepping face or a groove is provided on an end surface of the housing main body, the sealing strip is embedded in the stepping face or the groove and extends out of the end surface of the housing main body, surfaces of the first housing cover and/or the second housing cover close to the housing main body are pressed against onto a portion of the sealing strip extending out of the end surface of the housing main body; or, a stepping face or a groove is opened on edges of the first housing cover and/or the second housing cover, the sealing strip is embedded in the stepping face or the groove and extends out of the edges of the first housing cover and/or the second housing cover, the surfaces of the housing main body close to the first housing cover and/or the second housing cover are pressed against onto a portion of the sealing strip extending out of the edges of the first housing cover and/or the second housing cover.

And/or, the radiation device installation housing further comprises a collimator and one or more layers of the protection device(s) provided within the housing body, wherein:

The protection device is made in the material having shielding function to the X-ray; the collimator is integrated with the protection device, or, the collimator and the protection device are two separate components fixedly connected together; each layer of the protection device is provided with a ray exit, and the ray exit, the beam exiting hole and the beam exiting opening are coaxial.

Preferably, the projections are formed in annular, and a central axis thereof is coincident with a central axis of the flange.

And/or, the protection device is formed in cylindrical or prismatic shape, and the protection device includes a cylindrical body, a first end cap and a second end cap, wherein: the first end cap and the second end cap are respectively fixedly connected with two opposite ports of the cylindrical body; a fluid passage and/or a circuit passage are/is provided on one of the first end cap, the second end cap or the cylindrical body.

And/or, a layer of the protection device is provided in the housing body, a space through which liquid can flow and for installing the components are provided between the protection device and the housing body; or, a plurality layers of the protection devices are provided in the housing body, an inner layer of the protection device of the plurality layers of the protection devices is located within an outer layer of the protection device thereof, and spaces through which the liquid can flow and for installing the components are provided between the inner layer of the protection device and outer layer of the protection device as well as between an outmost layer of the protection device and the housing body.

And/or, the protection device is made of insulating materials.

And/or, a blocking window is filled in the beam exiting opening and is made in a material which the X-ray can penetrate, and the blocking window is used to achieve the liquid-air sealing between the inside and outside of the housing body.

Preferably, the protection device is made in lead oxidizes.

And/or, the fluid passage and/or the circuit passage are (is) a through hole or an angling hole having a bend shape at least opened on one of the first end cap, the second end cap or the cylindrical body; or at least one of the first end cap, the second end cap or the cylindrical body is a double layered structure configured by an outer layer plate and an inner layer plate laminated to each other, wherein:

A liquid flowing cavity is provided between the outer layer plate and the inner layer plate, and flow guiding holes in communication with the liquid flowing cavity are opened on both the outer layer plate and the inner layer plate, the fluid passage is constituted by the flow guiding holes and the liquid flowing cavity, an orthographic projection of the flow guiding hole along the axial direction thereof on the outer layer plate is completely staggered from the flow guiding hole on the inner layer plate.

Preferably, the protection device is made of lead tetroxide.

And/or, the fluid passage and the circuit passage are provided on both the first end cap and the second end cap.

And/or, an internal thread pipe is embedded in the cylindrical body, internal threads are provided within the internal thread pipe, a portion of a connection bolt opened with external threads is penetrated through the outer layer plate and engaged with the internal threads within the internal thread pipe, and fixedly connected with the cylindrical body and the first end cap as well as the second end cap together.

And/or, a positioning boss is fixed arranged on the inner layer plate, the positioning boss is inserted into a positioning counterbore on the outer layer plate and tightly mated with the positioning counterbore.

And/or, a stepping portion shaped as steps is provided on an edge at an inner side of the cylindrical body, the stepping portion is abutted against an edge of the inner layer plate.

And/or, at least one anode limit holes are opened on the inner layer plate of the second end cap, a limit screw hole is opened on the anode, an external thread portion engaged with the limit screw hole is opened on a positioning bolt, one end on the positioning bolt away from the limit screw hole is inserted into the anode limit hole.

And/or, a plurality of flow guiding holes are equiangularly distributed on the outer layer plate and/or inner layer plate on the first end cap and/or the second end cap in a circumferential direction of the cylindrical body, and the distance from each of the flow guiding holes to the central axis of the cylindrical body is equal.

And/or, a wiring hole on the outer layer plate in the first end cap includes a longitudinal hole being coincident coincident with or parallel to the axial direction of the cylindrical body and a transversal hole in communication with the longitudinal hole and an axial direction of the transversal hole being vertical to an axial direction of the longitudinal hole.

An X-ray radiator comprises an X-ray tube, a high frequency and high voltage generator, a filament power supply module and an oil cooling circulation system, wherein:

The X-ray tube is installed within the protection device, and the X-ray emitted from the X-ray tube in turn passes through the ray exit, the beam exiting hole and the beam exiting opening and radiates out of the housing body of the radiation device installation housing.

The high frequency and high voltage generator is electrically connected with the cathode and anode of the X-ray tube.

The filament power supply module is electrically connected with the cathode of the X-ray tube.

The oil cooling circulation system includes a liquid filling tank, an insulating liquid filled in the liquid filling tank and a cooling device used for reducing the temperature of the insulating liquid, the cooling device includes an oil pump, a radiator and a cooling fan, wherein:

The liquid filling tank is constituted by the radiator device installation housing provided in any one of above technical solutions in the present invention.

The radiator is located outside the liquid filling tank, and a liquid ingress of the radiator is in communication with a liquid exit of the liquid filling tank, a liquid egress of the radiator is in communication with a liquid entrance of the liquid filling tank.

The oil pump is used to provide power to the circulation flow between the insulating liquid within the liquid filling tank and the insulating liquid within the radiator.

The cooling fan is used to dissipate the heat on the radiator by ways of accelerating the air flowing around the radiator.

Preferably, a circuit passage is opened on the protection device, the high frequency and high voltage generator is electrically connected with the cathode and anode of the X-ray tube via conducting wires or interfaces passing through the circuit passage.

At least one part of modules constituting the high frequency and high voltage generator are located between the protection device and the housing body, and a housing external power supply or other part of modules constituting the high frequency and high voltage generator are located outside the housing body.

A wire exiting passage is opened on the housing body, the part of modules constituting the high frequency and high voltage generator located within the housing body are electrically connected with the other part of modules constituting the high frequency and high voltage generator located outside the housing body or the high frequency and high voltage is electrically connected with the housing external power supply through the conducting wires or interfaces passing through the wire exiting passage.

The protection device includes a cylindrical body, a first end cap and a second end cap, the first end cap and the second end cap are respectively fixedly connected with two ports of the cylindrical body.

A fluid passage and the circuit passage are opened on at least one of the first end cap, the second end cap or the cylindrical body.

Preferably, both the first end cap and the second end cap are a double layered structure formed by an outer layer plate and an inner layer plate laminated to each other together, and the circuit passages is provided on both the first end cap and the second end cap, wherein:

The circuit passage opened on the first end cap includes a cathode positioning hole opened on the inner layer plate on the first end cap and a wiring hole opened on the outer layer plate on the second end cap, a wire protection sleeve outside the cathode within the X-ray tube is embedded within the cathode positioning hole, the wiring hole includes a longitudinal hole coincident with or parallel to an axial direction of the X-ray tube and a transversal hole in communication with the longitudinal hole and an axial direction of the transversal hole being vertical to an axial direction of the longitudinal hole, the cathode of the X-ray tube is extracted out of the wiring hole through two conducting wires from the wire protection sleeve.

The circuit passage opened on the second end cap includes anode positioning holes opened on the inner layer plate and the outer layer plate of the second end cap, an electric conducting bolt in turn passes through the anode positioning holes opened on the outer layer plate and the inner layer plate of the second end cap, and an external thread portion opened on the electric conducting bolt is engaged with an anode screw hole opened on the anode, a positioning screw hole is opened on a portion of the electric conducting bolt away from the anode, and the external thread portion opened on an electric conducting screw is engaged with the positioning screw hole, and the conducting wires respectively electrically connected with the anode of the high frequency and high voltage generator are held between a head portion of the electric conducting screw and the electric conducting bolt.

And/or, a fluid passage is opened on both the first end cap and the second end cap, both the first end cap and the second end cap are a double layered structure formed by an outer layer plate and an inner layer plate laminated to each other together, a liquid flowing cavity is provided between the outer layer plate and the inner layer plate, and flow guiding holes in communication with the liquid flowing cavity are opened on both the outer layer plate and the inner layer plate, the fluid passage is formed by the flow guiding holes and the liquid flowing cavity.

The anode has a cover shape and covers at one end on a glass cover of the X-ray tube away from the cathode, a liquid flowing space is provided between the anode and a circumferential outer surface of the glass cover of the X-ray tube, liquid through holes respectively in communication with the liquid flowing space and the flow guiding holes on the inner layer plate on the second end cap are provided on the anode.

BRIEF DESCRIPTION OF THE DRAWINGS

The accompanying drawings described here will be made to provide a further understanding for the present invention and constitute a part of the present application; the following exemplary embodiments and the description thereof are used to explain the present invention and is not improper limitation thereto, wherein.

DETAILED DESCRIPTION OF THE EMBODIMENTS

Hereafter, the technical solution of the present invention is further described in detail through the accompanying drawings and following embodiments.

The embodiment of the present invention provides a radiation device installation housing which can effectively prevent the X-ray emitted from an X-ray tube from leaking to the periphery of the housing from the inside of the housing and an X-ray generator provided with the radiation device installation housing, wherein the radiation device installation housing has lighter weight and smaller footprint, and a compensation device (e.g. an elastic drum membrane) is easily mounted therein and the material for the compensation device is less.

Figure 1:
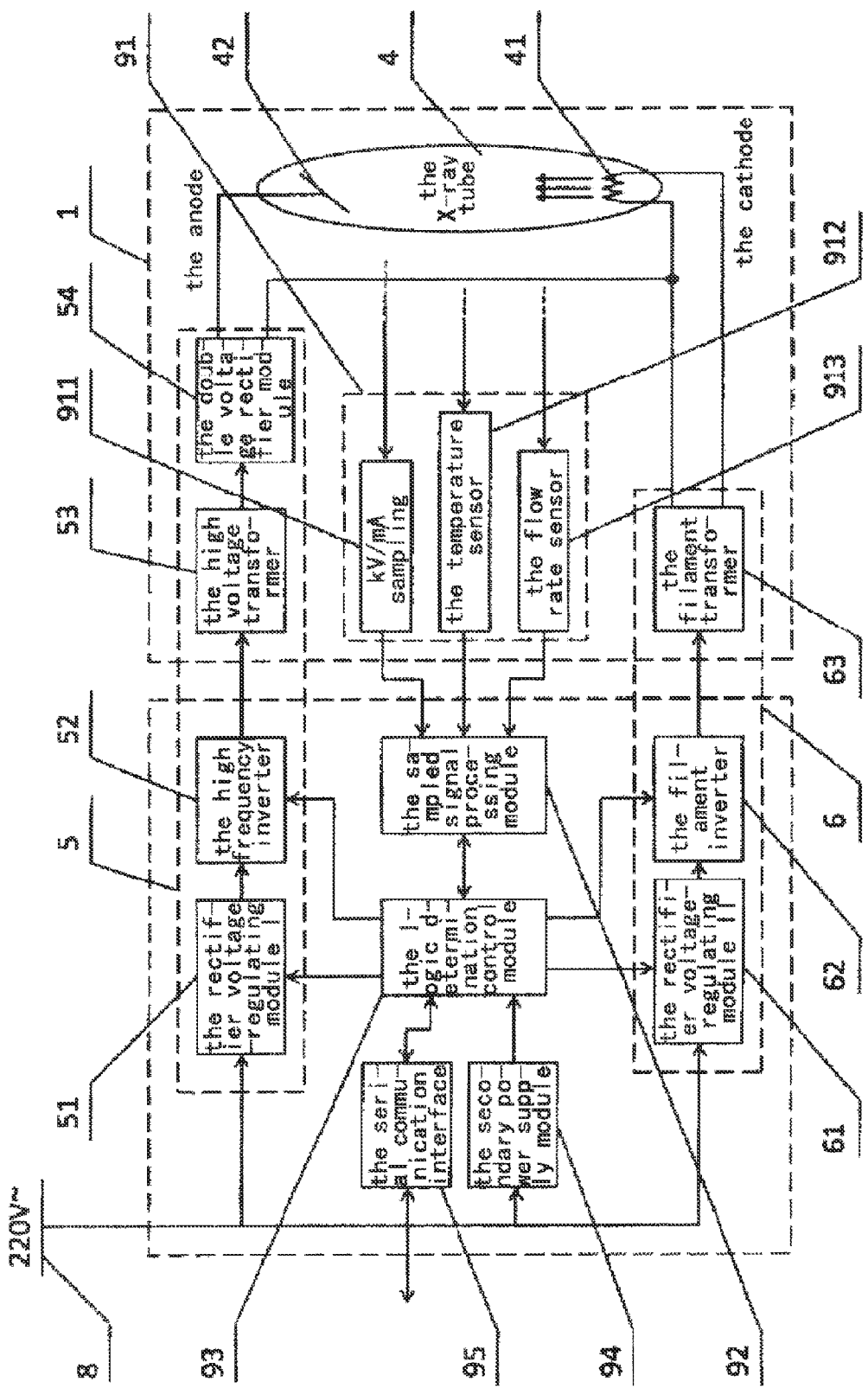
FIG. 1 is a schematic view of the connection relationships among each electronic element within an X-ray generator according to the embodiment of the present invention.
Figure 2:
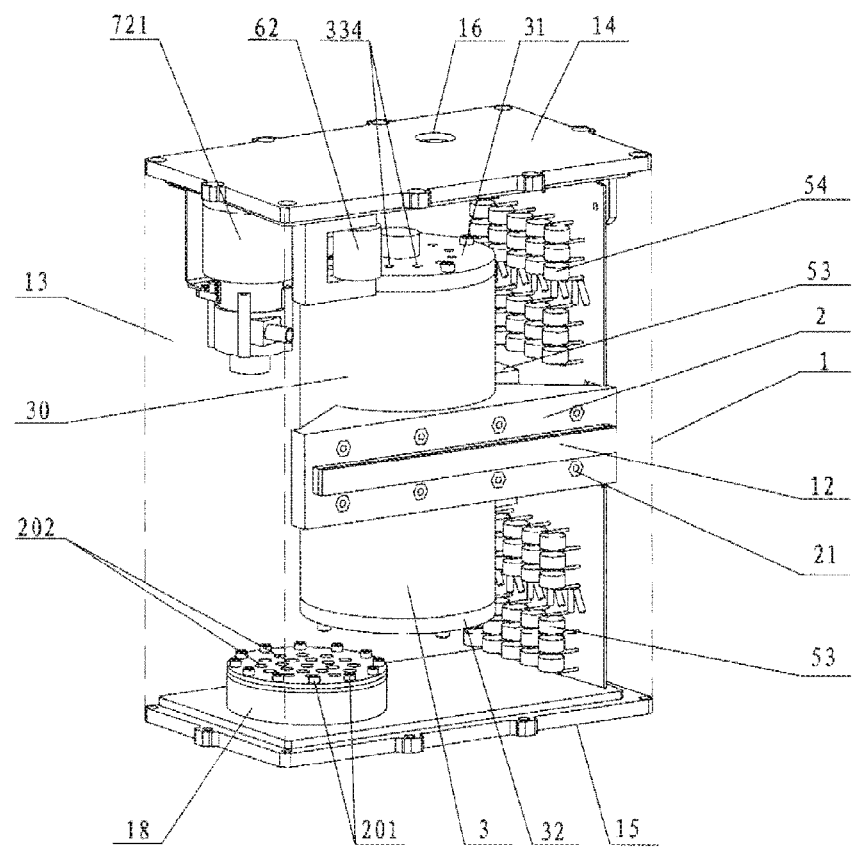
FIG. 2 is a perspective schematic view of partial components of the spatial structure of the radiation device installation housing according to the embodiment of the present invention.
Figure 3:
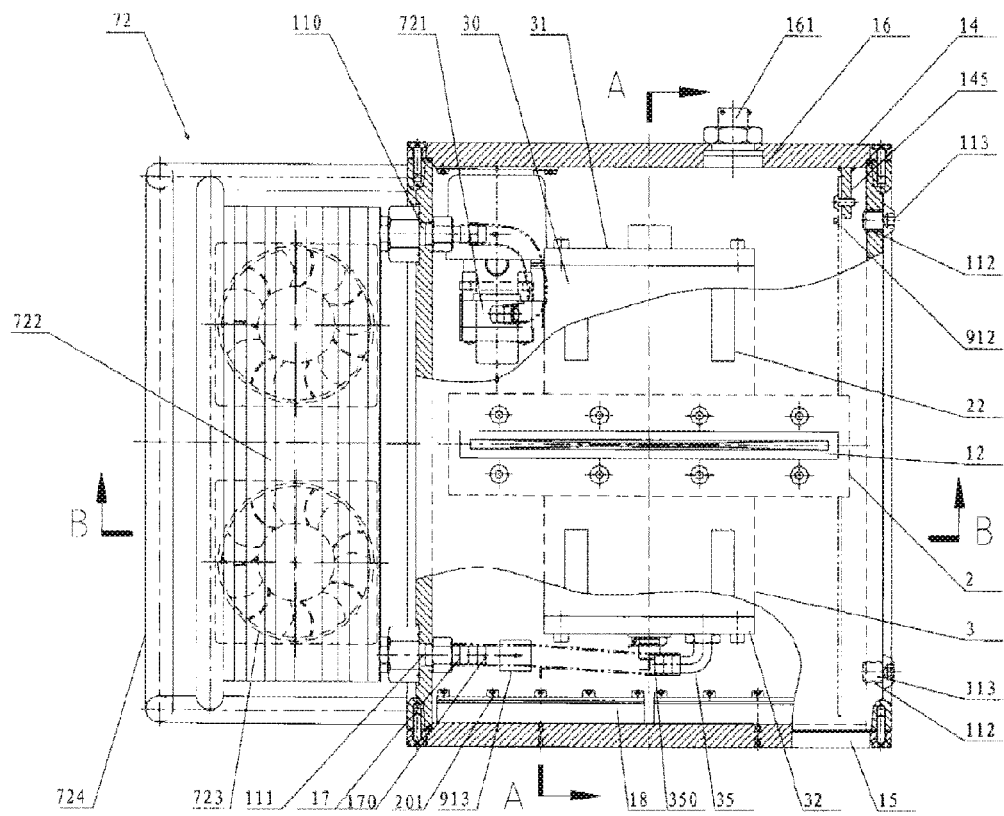
FIG. 3 is a partially cutaway upright view of the X-ray generator according to the embodiment of the present invention.

As shown in FIGS. 1, 2 and 3, the radiation device installation housing includes a housing body 1, a collimator 2 shown in FIG. 2, and a layer of protection device 3 located within the housing 1.

The layer of protection device 3 is made of the material shielding to the X-ray. A space for liquid flowing and mounting the components therein to be mounted therein is provided between the protection device 3 and the housing body 1. The collimator 2 and the protection device 3 are formed integrally. The collimator 2 and the housing body 1 are two separate parts and can be detachably connected together. The protection device 3 is opened with a ray exit 36 shown in FIG. 5, and the collimator 2 is opened with a beam exit aperture thereon (which coincides with the ray exit 36 in FIG. 5). The housing body 1 is provided with a beam exit opening 11 thereon, and the ray exit 36, the beam exit aperture and the beam exit opening 11 are coaxial.

Though the housing body 1 according to the embodiment of the present invention is provided with a layer of protection device 3 therein, as a variation, a plurality of layers of protection device 3 can be provided. The protection device 3 is made of materials shielding to the X-ray (for example, lead oxides), and the protection device 3 is located within the housing body 1. When the X-ray tube 4 shown in FIG. 5 is located in the protection device 3, the X-ray emitted from the X-ray tube 4 is in turn passed through the ray exit 36, the beam exit aperture and the beam exit opening 11 being coaxial shown in FIG. 5 and emitted out of the housing body 1.

In the present embodiment, the ray exit 36, the beam exit aperture and the beam exit opening 11 can be coaxial all together, that is, all orthographic projections thereof along their respective axial direction are fully coincident with each other. It also means that they can be partially coaxial, that is, the orthographic projections thereof along their respective axial direction are partially coincided. No matter the ray exit 36, the beam exit aperture and the beam exit opening 11 are fully coaxial or partially coaxial, it will work as long as the X-ray can be in turn passed through the ray exit 36, the beam exit aperture and the beam exit opening 11 and finally emitted out of the housing body 1.

As shown in FIG. 2 in the present embodiment, a space for liquid flowing and mounting the components therein is disposed between the protection device 3 and the housing body 1, the size of the space can be provided according to the requirement. On one hand, the space for liquid flowing and mounting the components can be used for mounting the electrical elements, filling the insulating liquid for increasing the insulation properties and heat radiation properties between the electrical members, on the other hand, the protection device 3 can be made smaller under the condition that the thermal dissipation and protection effects are not affected, so that the production materials can be saved and the volume and the weight of the housing body can be reduced.

Figure 5:
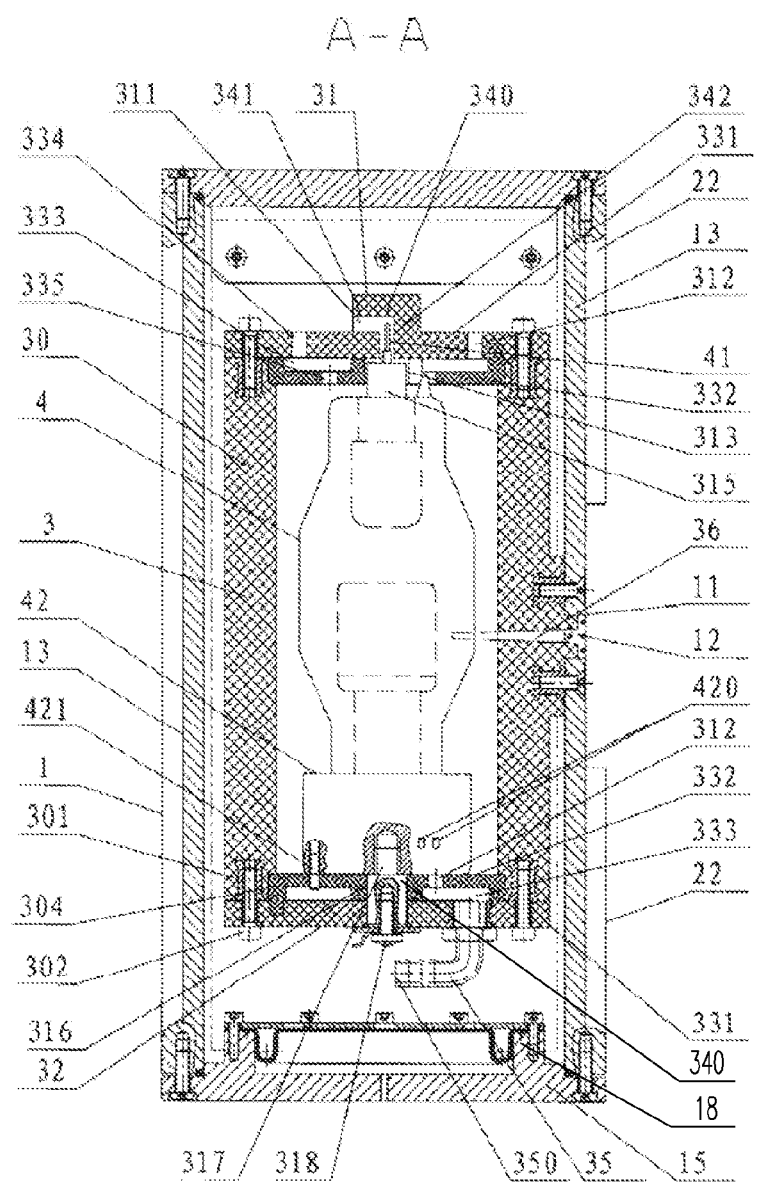
FIG. 5 is a sectional view taking along line A-A of FIG. 3.

When the X-ray tube 4 shown in FIG. 5 can be mounted in the protection device 3 within the housing body 1, the thickness of the protection device 3 and the number of layers of the protection device 3 (the number is one when one layer of the protection device 3 is provided) can be determined based on the intensity of the X-ray emitted from the X-ray tube 4.

When the plurality of layers of the protection devices 3 are provided within the housing body 1, each layer of the protection device 3 can be made of the material shielding to the X-ray. Also, a part of layers of the plurality of layers of the protection devices 3 are made of the material shielding to the X-ray. Each layer of the protection device 3 is located within the housing body 1, the inner layer of the protection device 3 is located inside the outer layer of the protection device 3. A space for liquid flowing and mounting the components is provided between the housing body 1 and the outmost layer of the protection device 3, and the X-ray tube 4 is mounted within the most inner layer of the protection device 3.

Additionally, in the embodiment of the present invention, the collimator 2 and the housing body 1 can be formed integrally, at this time, the collimator 2 and the protection device 3 can be two separated parts detachably fixedly connected together (for example, fixedly connected by using screws and bolts). Certainly, under the condition of higher precision of the production, the collimator 2, the housing body 1 and the protection device 3 or the main bodies thereof can be formed integrally.

Figure 9:
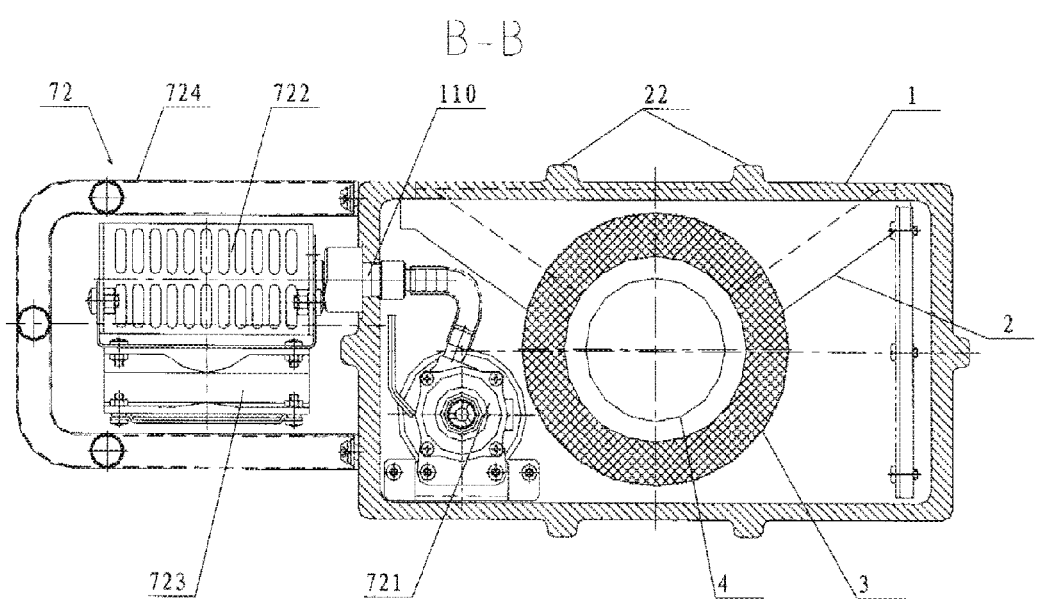
FIG. 9 is a sectional view taking along line B-B of FIG. 3.

As shown in FIGS. 2, 5, and 9, in the present embodiment, the protection device 3 is formed in cylindrical shape which includes a cylindrical body 30, a first end cap 31 and a second end cap 32, the first end cap 31 and the second end cap 32 are fixedly connected with two ports of the cylindrical body 30, and the first end cap 31 and the second end cap 32 are opened with a fluid passage 312 and a circuit passage 311 thereon shown in FIG. 5.

The above structure is simple, so it is not only convenient for assembling the protection device 3, which is convenient for manufacturing the components of the protection device 3, but also convenient for the insulating liquid smoothly flowing and building-up and formulating of the wires and interfaces. Since the insulating liquid is smoothly flowing, when the X-ray tube 4 is mounted within the protection layer 3, it will be advantageous for dissipating the heat from the X-ray tube 4 mounted within the protection device 3, so that the cooling efficiency of the X-ray tube 4 is increased. In addition to the cylindrical shape, the protection device 3 also can be formed in prismatic shape (including cuboid and square), frustum cone shape or other shapes.

As shown in FIG. 5, in the present embodiment, one or both the circuit passage 311 and the fluid passage 312 can be only provided on the cylindrical body 30. Certainly, the circuit passage 311 and the fluid passage 312 also can be provided on the cylindrical body 30 as well as the first end cap 31 or the second end cap 32, respectively.

As shown in FIG. 5, in the present embodiment, both the first end cap 31 and the second end cap 32 are a double layered structure formed by an outer layer plate 331 and an inner layer plate 332 laminated to each other, wherein:

A liquid flowing cavity 333 is provided between the outer layer plate 331 and the inner layer plate 332, and a flow guiding hole 334 being in communication with the liquid flowing cavity 333 is opened on the outer layer plate 331, and a flow guiding hole 335 being in communication with the liquid flown cavity 333 is opened on the inner layer plate 332. The fluid passage 312 is composed of the flow guiding hole 334, the flow guiding hole 335 and the liquid flowing cavity 333, and the orthographic projection of the flow guiding hole 334 along the axial direction thereof on the outer layer plate 331 is completely staggered from the flow guiding hole 335 on the inner layer plate 332.

In the present embodiment, the circuit passage 311 opened on the first end cap 31 includes a cathode positioning hole 313 provided on the inner layer plate 332 of the first end cap 31 and a wiring hole 340 provided on the outer layer plate 331 on the first end cap 31. The wiring hole 340 is a through hole being shape of bent. The wiring hole 340 preferably includes a longitudinal hole 342 being coincident or parallel with the axial direction of the protection device 3 and a transversal hole 341 being in communication with the longitudinal hole 342 and the axial direction thereof being vertical to the axial direction of the longitudinal hole 342.

When the housing body 1 is filled with the insulating liquid, the first end cap 31 and the second end cap 32 in the above structure can both ensure that the insulating liquid can flow into the cylindrical body 30 through the fluid passage 312 on the second end cap 32 and flow out of the protection device 3 through the first end cap 31. It is more important that when the X-ray tube 4 is mounted within the protection device 3, the orthographic projection of the flow guiding hole 334 on the outer layer plate 331 along the axial direction thereof is completely staggered from the flow guiding hole 335 on the inner layer plate 332. The fluid passage 312 forms a labyrinth structure, although the X-ray emitted from the X-ray tube 4 passes through the flow guiding hole 335 on the inner layer plate 332, it would not pass through the flow guiding hole 334 on the outer layer plate 331, thereby, the X-ray is not penetrated through the protection device 3. And similarly, the circuit passage 311 in above structure is also formed in a labyrinth structure, so that while the circuit passage 311 does not interfere with the built-up of the interfaces and the conducting wires, the X-ray directly passing through the protection device 3 can be effectively shielded.

In the present invention, in order to allow the circuit passage 311 and/or the fluid passage 312 to form in the labyrinth structure described above, the first end cap 31 and the second end cap 32 can be not provided into the double layered structure. At this time, the circuit passage 311 and/or the fluid passage 312 can be a through hole in bent shape (for example, a folding line with a right angle) or an angling hole (for example, an acute angle or an obtuse angle is disposed between the axial direction of the angling hole and the axial direction of the protection device 3, preferably the acute angle with a smaller angle value or the obtuse angle with a larger angle value).

Certainly, one of the flow guiding hole 334 on the outer layer plate 331 or the flow guiding hole 335 on the inner layer plate 332 and/or one of the wiring hole 340 on the outer layer plate 331 or the wiring hole 340 on the inner layer plate 332 can also be the through hole shaped in bent (for example, a folding line with a right angle) or the angling hole, and at this time, the first end cap 31 and the second end cap 32 also can form the circuit passage 311 and/or the fluid passage 312 with the labyrinth structure. Since the orthographic projections of two ports of the angling hole on the radial direction of the protection device 3 are completely or partially staggered, the angling hole also can block the x rays partially or completely emitting to one port of both ports of the angling hole from passing out of the another port thereof while realizing the leading path or flowing the insulating liquid, more particularly, when the ratio of the thickness of the protection device 3, the first end cap 31 and the second end cap 32 to the port size(s) of the circuit passage 311 and/or the fluid passage 312 is larger.

Figure 6:
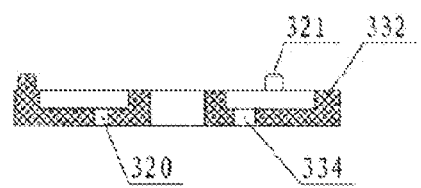
FIG. 6 is a sectional view of the inner layer plate of the first end cap in FIG. 5.
Figure 7:
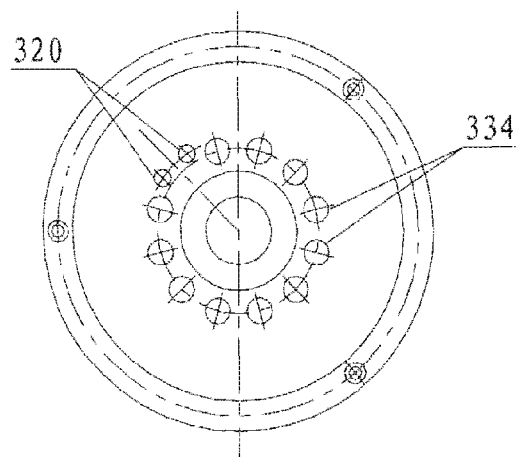
FIG. 7 is a top view of the inner layer plate of the first end cap in FIG. 6.

As shown in FIG. 5, in the present embodiment, a plurality of (more than two) flow guiding holes 335 are equiangularly distributed in the circumferential direction of the cylindrical body 30 shown in FIG. 5 on the inner layer plate 332 shown in FIGS. 6 and 7 provided on the first end cap 31, and the distances of each flow guiding hole 335 from the axis of the cylindrical body 30 (which is also the axis of the protection body 3) are the same.

Certainly, a plurality of (more than two) flow guiding holes 334 are equiangularly distributed in the circumferential direction of the cylindrical body 30 on the outer layer plate 331 provided on the first end cap 31. The flow guiding holes 335 can be distributed on the first end cap 31 in other arrangement. Meanwhile, the flow guiding holes 334 on the first end cap 31 also can be distributed in the above manner. Further, the flow guiding holes 334 or 335 can be distributed on only one of the outer layer plate 331 or the inner layer plate 332 of the first end cap 31 in above manner.

In the present embodiment, since the wiring hole 340 on the outer layer plate 331 within the first end cap 31 includes the longitudinal hole 342 coinciding with the axial direction of the cylindrical body 30 (which is also the axial direction of the protection device 3) and the transversal hole 341 being in communication with the longitudinal hole 342 and the axial direction thereof being vertical to the axial direction of the longitudinal hole 342.

The transversal hole 341 and the longitudinal hole 342 form the wiring hole 340 having a folding line shape with a right angle, such formation is able to ensure that while the conducting wire (which can be treated as a part of the cathode 41) electrically connected with the cathode 41 of the X-ray tube 4 is extracted from the wiring hole 340, the X-ray emitted from the X-ray tube 4 does not penetrate out from the wiring hole 340. Of course, the longitudinal hole 342 also is parallel with the axial direction of the cylindrical body 30, and the wiring hole 340 can be the angling hole or the through hole having other bend shapes (for example, a folding line shape having an acute angle or an obtuse angle)

A wire protection sleeve 315 of the X-ray tube 4 for protecting the cathode 41 is embed into the cathode positioning hole 313 of the inner layer plate 332 within the first end cap 31, and the conducting wire protection sleeve 315 (typically being made of copper material) electrically connected with the cathode 41 leads the protection device 3 out. The anode 42 (or the anode base) within the X-ray tube 4 is fixed onto the second end cap 32 by using fasteners made in electric conductive material (in the present embodiment, the electric conducting bolt 317 and the electric conducting screw 318 shown in FIG. 5 can be used as the fasteners), and the anode 42 of the X-ray tube 4 is electrically connected with the anode of the double voltage rectifier module 54, which is also the anode of the high frequency and high voltage generator 5, outside the protection device 3 through the fasteners 317 and 318 and the conducting wire electrically connected with the fasteners 317 and 318. The fasteners 317 and 318 made of the electric conducting materials have the electric conductive function per se.

The anode 42 of the X-ray tube 4 is shaped like a cover and covers at one end on the glass cover of the X-ray tube 4 away from the cathode 41, a liquid flowing space 422 is provided between the anode 42 and the circumferential outer surface of the glass cover of the X-ray tube 4, and a liquid passing hole 423 being in communication with the liquid flowing space 422 is opened on the anode 42. In such arrangement, the insulating liquid outside the protection device 3 is flown into or out of the protection device 3 through the liquid passing hole 423 shown as FIG. 12 or FIG. 13. In the present embodiment, the axial direction of the liquid passing hole 423 is preferably parallel to the axial direction of the X-ray tube 4.

In order to more efficiently position the anode 42, one or two or more circumferential screw holes 420 are provided on the circumferential outer surface of the anode 42, the anode 42 is fixed within the protection device 3 in the circumferential direction of the anode 42 by the screws passing through the cylindrical body 30 and threaded into the circumferential screw holes 420.

The above configuration has advantages in easy installation, and good reliability in connection.

The number of the flow guiding holes 355 distributed on the inner layer plate 332 provided on the first end cap 31 is preferably equal to number of the liquid passing holes 423 on the anode 42 within the X-ray tube 4; however, two numbers of them can also be different. The above configuration facilitates that the insulating liquid with the lower temperature is firstly flown into the vicinity of the anode 42 within the X-ray tube 4, so that the target embedded into the anode 42 of the X-ray tube 4 is prevented from the damage due to the significantly high temperature thereof.

In the present embodiment, the protection device 3 is made of the material having both protection and insulation performance. Since when the X-ray tube 4 is mounted within the protection device 3, the above configuration allows to efficiently prevent both the X-ray from leakage, and the X-ray tube 4 applied with the high voltage and the electrical elements or modules (for example, the high voltage adaptor 53, the double voltage rectifier module 53 within the high frequency and high voltage generator 5 shown in FIG. 1) supplying high voltage to the X-ray tube 4 from the failure due to sparking or the short circuit in the housing 1.

In the present embodiment, an internal thread pipe 301 is embedded into the cylindrical body 30, and internal threads are provided within the internal threading tube 301. The portion of the connection bolt 302 opened with external threads is penetrated through the outer layer plate 331 and engaged with the internal threads within the internal thread pipe 301, and fixedly connected with the first end cap 31 and the second end cap 32.

The threading connection structure constituted by the connection bolt 302 and the internal thread pipe 301 fixedly connects the first end cap 31 and the second end cap 32.

Since the cylindrical body 30 is made of lead oxides, it is very brittle and is difficult to produce the internal threads by using the cutting technology. Since the embedded internal thread pipe 301 is preferably made of metal material with high temperature resistance, it can be embedded into the produced cylindrical body 30 before the cylindrical body 30 is completed.

In the present embodiment, as shown in FIG. 6, a positioning boss 321 is fixedly arranged on the inner layer plate 332 and is inserted into a positioning counterbore (not shown) on the outer layer plate 331 and tightly mated with the positioning counterbore. Preferably, the positioning boss 321 and the inner layer plate 332 are formed integrally.

In the present embodiment, a stepping portion 304 shaped as steps are provided on the edge at the inner side of the cylindrical body 30, and the stepping portion 304 is abutted against the edge of the inner layer plate 332. The above configuration has advantages in easy installing, convenient assembling and impact structure.

Figure 10:
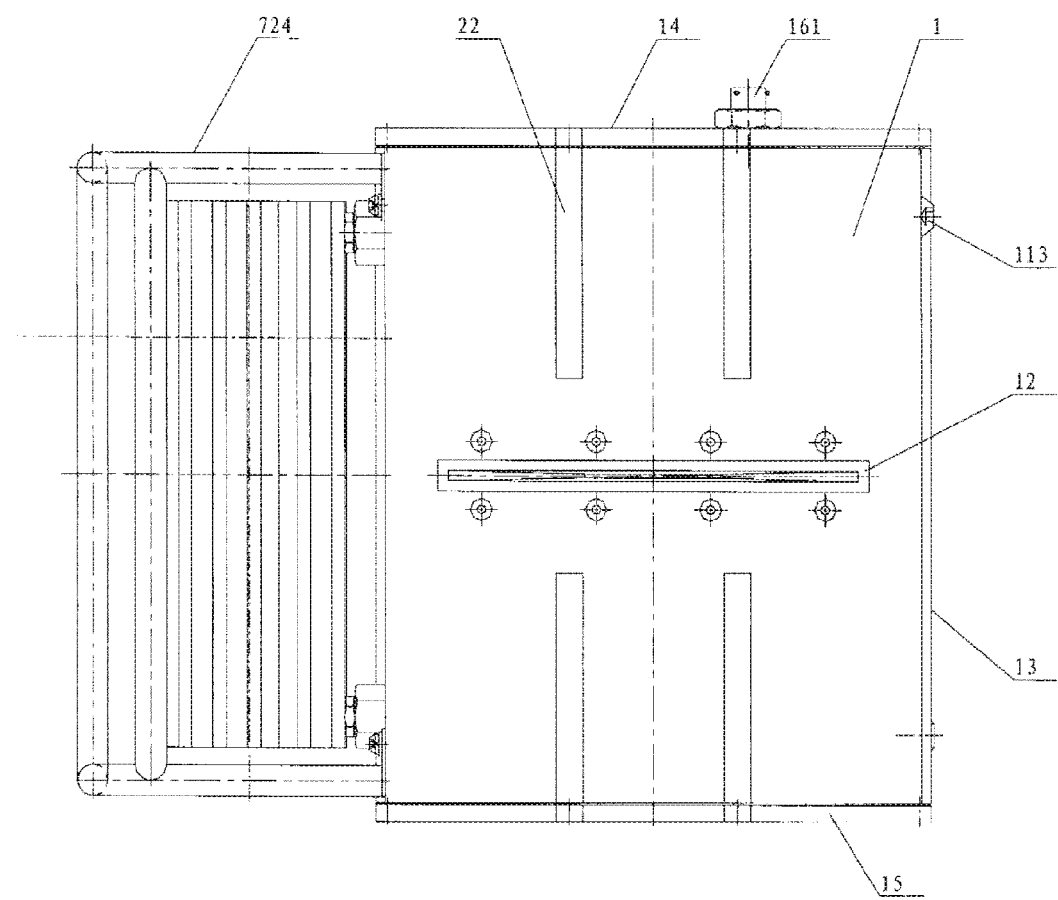
FIG. 10 is an upright schematic view of the radiation device installation housing according to the embodiment of the present invention.

As shown in FIG. 5, in the present embodiment, a blocking window 12 as shown in FIG. 3 or 10 is filled in the beam exit opening 11. The blocking window 12 can be made of the material which the X-ray can penetrate, and has the function of achieving the liquid seal and gas seal between the inside and outside of the housing body 1.

The blocking window 12 seals the beam exit opening 11, on one hand, the air or the dust outside the housing is prevented from entering into the housing body 1, on the other hand, when the insulating liquid is filled in the space for flowing the liquid and installing the components within the protection device 3 and/or between the protection device 3 and the housing body 1, the blocking window 12 can prevent the insulating liquid from leaking out of the housing body 1 from the beam exit opening 11. When the insulating liquid is filled in the protection device 2, the X-ray emitted from the X-ray tube 4 will penetrate through the insulating liquid and radiate to the outside of the housing body 1 from the blocking window 12. Since the X-ray emitted from the X-ray tube 4 has high intensity, the loss of the X-ray caused by the insulating liquid is extremely small, and usually it can be ignored.

Of course, it is possible to not provide the blocking window 12 in the present invention. When the glass cover of the X-ray tube 4 shown in FIG. 5 and the ray exit 36 on the protection device 3 are closely abutted against the port within the protection device 3, and the ray exit 36, the beam exit hole (coincide with the ray exit 36), the beam exit opening 11 and the glass cover of the X-ray tube 4 are configured into an insulating liquid seal chamber, the insulating liquid cannot be leaked through the gap between the X-ray tube 4 and the protection device 3 to the ray exit 36, the beam exit hole and the beam exit opening 11.

In the present embodiment, the insulating material preferably is lead tetraoxide. The sheet or the container made of lead tetraoxide has a stronger shielding function to the X-ray. Of course, the insulating material also can be made of other lead oxides in addition to lead tetraoxide, comparing to the lead or lead-antimony alloy and so on having a stronger shielding function to the X-ray, the lead oxides has advantages such as low density, high strength, and good electrical insulation performance and radiation protection performance.

As shown in FIGS. 5 and 10, the housing body 1 in the present embodiment includes a housing main body 13, a first housing cover 14 and a second housing cover 15, wherein the first housing cover 14 and the second housing cover 15 are respectively fixedly arranged on both ports of the housing main body 13 that has an integrated structure, and the material for producing the first housing cover 14 and the second housing cover 15 is the same as that of the housing main body 13.

The integrated housing main body 13 not only has a simple structure, good connection strength between each part, convenient one-step molding technology for the production, but also has better seal effect provided by the integrated housing main body 13 in respect to the housing main body 13 formed by splicing sheet materials (typically by using the screw connection or welding). The housing body 1 is more excellent at the leakage protection performance to the insulating liquid and the X-ray, and in the meanwhile, during the process of using the X-ray generator, particularly, when the insulating liquid is injected into the housing body 1 in a vacuum oil-injection manner (after the insulating liquid is injected by using the vacuum oil-injection method via an oil injection hole 112 shown in FIG. 3, then the oil injection hole 112 is sealed by using a seal packing and a seal bolt 113), the air outside the housing body 1 will not be permeated through the housing main body 13 into the inside of the housing body 1, so that the influences of the air on the heat dissipation of the insulating liquid and the insulation effect are avoided. Certainly, the housing main body 13 also can be formed by splicing individual separate structures via welding or threaded connection, and at this time, the material for producing the first end cover 14, the second end cover 15 and the housing body 13 can be different.

Figure 4:
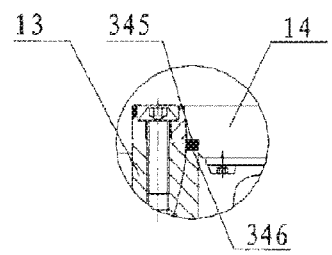
FIG. 4 is an enlarge view of the portion in FIG. 3 provided with a sealing strip.

In the present embodiment, as shown in FIGS. 3, 4, and 5, sealing strips 345 (shown in FIG. 5) made of rubber material are provided between the first housing cover 14 and the housing main body 13 as well as between the second housing cover 15 and the housing main body 13, wherein:

A stepping face 346 as shown in FIG. 4 or a groove is opened on the end surface of the housing main body 13, the sealing strips 345 are embedded in the stepping face 346 or the groove and extended out of the end surface of the housing main body 13, and the first housing cover 14 and the second housing cover 15 in the proximity of the surface of the housing body 13 are pressed against onto the sealing strips 345.

In such configuration, the sealing strips interposed between the first housing cover 14 and the housing main body 13 as well as between the second housing cover 15 and the housing main body 13 are pressed, so the contacts between the sealing strips 345 and the first housing cover 14 as well as the housing main body 13 are more tight which causes a better sealing effect.

In above configuration, the sealing strips 345 is also made of other elastic material in addition to the rubber material, and the location thereof can be not only positioned between the first housing cover 14 and the housing main body 13 or between the second housing cover 15 and the housing main body 13.

Certainly, as shown in FIG. 4, the stepping face 346 or the groove also can be provided at the edges of the second housing cover 15 shown in FIG. 5 and/or the first housing cover 14, at this time, the sealing strips 345 are embedded within the stepping face 346 or the groove and extended out of the edges of the first housing cover 14 and/or the second housing cover 15, the housing main body 13 in the proximity of the surfaces of the first housing cover 14 and/or the second housing cover 15 is pressed against onto the sealing strips 345.

In the present embodiment, as shown in FIG. 5, the housing main body 13 is made of the aluminum or the aluminum-alloy materials with high strength and light weight by employing stretching process. The production efficiency of the stretching process is high, and at the same time, the leakage easily caused by the deformation or disfigurement of the welding structure can also be avoided. Indeed, the housing body can be made in other materials or with the linear cutting process and so on.

In general, in this embodiment, the housing body 1, which is made of aluminum alloy with the stretching process, and the protection device 3 are superior to those produced by employing the traditional technology in the volume and the weight. Thus the radiation device installation housing provided in the present embodiment also has other advantages such as having light weight, being convenient for processing, assembling and carrying and the like.

Figure 8:
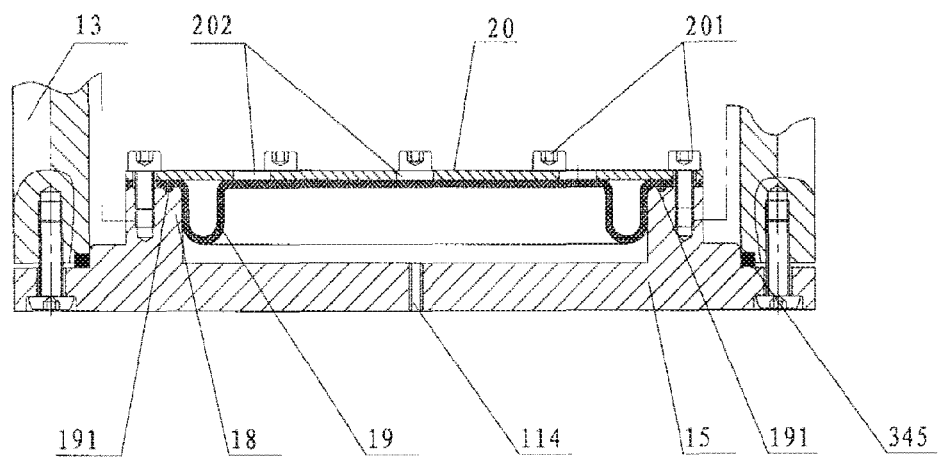
FIG. 8 is an enlarged sectional view of a concave edge, an elastic drum membrane and a connection of the second housing cover shown in FIG. 5.
Figure 11:
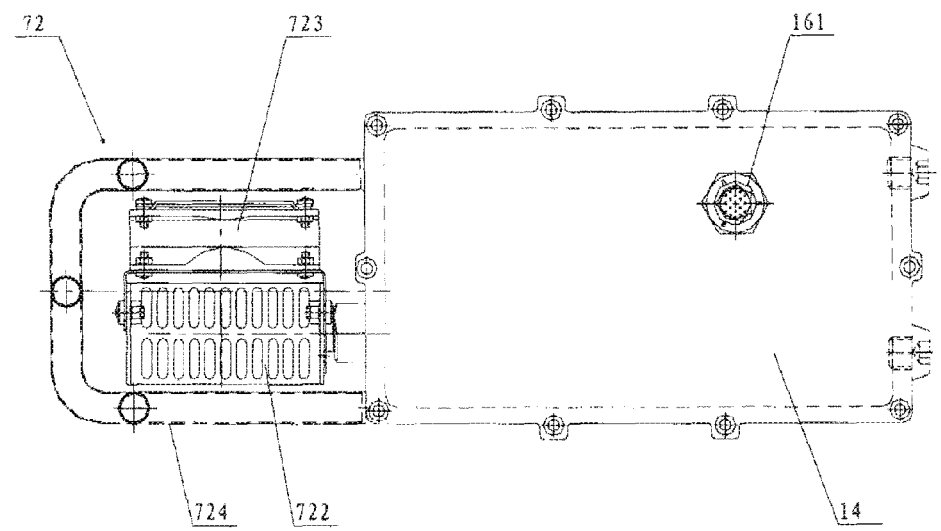
FIG. 11 is a top view of the radiation device installation housing shown in FIG. 9.

As shown in FIGS. 8 and 11, the oil cooling circulation system provided in the present embodiment comprises a liquid filling tank, the insulating liquid for filling into the liquid filling tank, and a cooling device 72 including an oil pump 721, a radiator 722 and a cooling fan 723 for decreasing the temperature of the insulating liquid.

The liquid filling tank is constituted by the radiation device installing housing provided in the embodiment of the present invention. The radiator 722 is positioned at the outside of the liquid filling tank, and a liquid ingress of the radiator 722 is in communication with a liquid exit of the liquid filling tank, and a liquid egress of the radiator 722 is in communication with a liquid entrance of the liquid filling tank. The oil pump 721 supplies the power to the circulation flowing between the insulating liquid within the liquid filling tank and the insulating liquid within the radiator 722. The cooling fan 723 releases the heat on the radiator 722 in the manner of accelerating the air flown around the radiator 722.

In this embodiment, the insulating liquid is 25# transformer insulating oil according to the Chinese national standard on transformer insulating oil. The insulating liquid is not only served as the insulating medium to avoid the sparking through or short circuit fault occurred in a variety of the elements or modules loaded with the high voltage, but also has the function of the heat radiating medium. Indeed, the insulating liquid also can employ other insulating oils in addition to 25# transformer insulating oil.

The X-ray tube 4 only can convert about 1% of the energy into the X-ray, and the remaining about 99% of energy is totally converted into the thermal energy and is applied into the anode 42 of the X-ray tube 4. Thus, in order to prevent the anode 42 of the X-ray tube 4 from overheating which will cause the target to melt down and damage, it is necessary to achieve the heat radiating effect by externally connecting the oil pump 721, performing the oil circulation cooling via the radiator 722, and allowing the cooled insulating liquid to finally backflow to the anode 42 of the X-ray tube 4.

In this embodiment, as shown in FIG. 1, the housing external power supply 8 is 220V alternate utility power, of course, the housing external power supply 8 also can be the power supply or the storage battery usually used in the factory.

The insulating liquid freely flown within the protection device 3 and between the housing 1 and the protection device 3 through the fluid passage 312 shown in FIG. 5 will transfer the heat (the heat is mainly produced by the anode 42 of the X-ray tube 4) produced by the X-ray tube 4 shown in FIG. 5 into the radiator 722, and then the heat is released by the flown air. Then, the insulated liquid cooled by the radiator 722 is fed into the protection device 3 as well as between the housing 1 and the protection device 3 again, and absorbs the heat produced by the X-ray tube 4 again.

When designing the cooling system, not only the heat radiating efficiency of the housing body 1, the protection device 3, the radiator 722 and the insulating liquid is considered, but also the power consumption of the oil pump 721 shown in FIG. 3 or FIG. 9 is considered, so that the cooling system of which the radiating performance meets with the overall radiating requirements of the X-ray generator is designed.

Of course, the power for the circulation flowing between the insulating liquid within one of the protection device 3 or the housing body 1 and the insulating liquid within the radiator 722 also can be provided by the oil pump 721.

As shown in FIGS. 3 and 9, in this embodiment, the oil pump 721 is fixedly arranged on the inner wall of the housing body 1 (preferably the oil pump 721 is fixedly arranged on the first housing cap 14 by using a screw or a bolt), and is located between the housing body 1 and the protection device 3. The installation space between the housing body 1 and the protection device 3 is plenty and is adapted for installing the oil pump 721.

In the present embodiment, a liquid suction opening of the oil pump 721 shown in FIG. 3 is oriented toward a liquid outlet of the protection device 3. A liquid inlet of the protection device 3 is in communication with a liquid ingress pipe 35. A liquid entering opening 111 of the body 1 is in communication with a liquid entering pipe 17. A liquid exiting port 170 of the liquid entering pipe 17 is oriented toward a liquid ingress port 350 of the liquid ingress pipe 35.

In such configuration, the insulating liquid having more heat has been sucked from the liquid outlet of the protection device 3 by the oil pump 721, and transferred from the liquid exiting opening 110 (show in the FIG. 3) of the housing body 1 to the radiator 722. The flowing of the insulating liquid can be more unrestricted by providing pipes, the liquid ingress pipe 35 and the liquid entering pipe 17.

Of course, in above configuration, the liquid suction opening of the oil pump 721 also can be in communication with the liquid outlet of the protection device 3 and/or the liquid exiting port 170 of the liquid entering pipe 17 can be in communication with the liquid ingress port 350 of the liquid ingress pipe 35 via pipes. The oil pump 721 also can be fixedly arranged within the radiator 722, or partially between the liquid filling tank and the protection device 3 and partially fixedly arranged within the radiator 722. When the number of the oil pump 721 is more than two, one or several of the oil pumps can be located within the radiator 722, and the other one or several of the oil pumps can be located between the liquid filling tank and the protection device 3.

As shown in FIG. 3 or FIG. 9, the oil pump 721 of the present embodiment is a DC brushless submersible pump which has advantages in excellent sealing, low noise, lower power consumption, stable performance, and long life span.

Of course, the cooling fan 723 shown in FIG. 9 also can employ a direct refrigeration manner for the radiator 722 by using other refrigerating devices (such as the refrigerating devices used in the refrigerator or freezer) instead of employing the air cooling manner. As shown in FIGS. 9 and 10, the cooling device 72 in the present embodiment also comprises a bracket 724 in the frame shape covered outside of the radiator 722 and the cooling fan 723, and the bracket 724 is fixedly connected with two separate parts of the housing body 1.

The bracket 724 is produced by welding the aluminum alloy material pipes with small density, the structure of the bracket 724 consumes less material, which not only can protect the radiator 722 and the cooling fan 723, but also can be served as a handle for easily moving the device by the user.

Of course, the bracket 724 also can be either produced by employing other materials, or by welding the solid rods or connecting the joint structure constituted by a bolt or a screw and a screw holes on the rod. The bracket 724 also can be replaced by other shielding covers with a good ventilation effect.

As shown in FIGS. 1 and 2, the X-ray generator provided in the embodiment of the present invention includes the X-ray tube 4, the high frequency and high voltage generator 5, the filament power supply module 6 and the oil cooling circulation system provided in above any embodiment of the present invention. The X-ray tube 4 is mounted within the protection device 3 inside the radiation device installing housing, and the X-ray emitted from the X-ray tube 4 in turn passes through the ray exit 36, the beam exit hole (coincides with the ray exit 36) and the beam exit opening 11 and is radiated out of the housing body 1 of the radiation device installation housing.

The high frequency and high voltage generator 5 is electrically connected with the cathode 41 and the anode 42 of the X-ray tube 4 and is used to supply the DC voltage thereto. The filament power supply module 6 is electrically connected with the cathode 41 of the X-ray tube 4 and is used to supply the high frequency pulse voltage, which is enough to allow the cathode 41 of the X-ray tube 4 to emit the current flow bombarding to the anode 42 under the high voltage electric field, for the cathode 41 of the X-ray tube 4.

The circuit passage 311 shown in FIG. 5 is also provided on the protection device 3 in the present embodiment. As shown in FIG. 1, the cathode of the high frequency and high voltage generator 5 is electrically connected with the cathode 41 of the X-ray tube 4 via the conducting wire passing through the circuit passage 311, and the anode of the high frequency and high voltage generator 5 is electrically connected with the anode 42 of the X-ray tube 4 via the conducting wire electrically connecting with the electric conducting screw 318 and the electric conducting bolt 317. The filament power supply module 6 is electrically connected with the cathode 41 of the X-ray tube 4 via the conducting wire passing through the circuit passage 311.

A part of the modules constituting the high frequency and high voltage generator 5 is located between the housing body 1 and the protection device 3, and the housing external power supply 8 and the other part of the modules constituting the high frequency and high voltage generator 5 are located outside the housing body 1. A wire exiting passage 16 shown in FIG. 3 is provided on the housing body 1, and the part of the modules within the housing body 1 and the other part of the modules outside the housing body 1 of the high frequency and high voltage generator 5 shown in FIG. 1 are electrically connected through the interfaces of the wire exiting passage 16.

Of course, all of modules constituting the high frequency and high voltage generator 5, which is, the whole of the high frequency and high voltage generator 5, the sampled signal processing module 92 and the logic determination control module 93 also can be provided between the housing body 1 and the protection device 3. At this time, above electric devices are electrically connected between the external power supply circuit and the remote communication signal emitting circuit required by those electric devices through the interfaces of the wire exiting passage 16. The conducting wires used for above electrical connection can be replaced by the interfaces, and the interfaces also can be replaced by the conducting wires.

Furthermore, in the present embodiment, the portion of the modules constituting the high frequency and high voltage generator 5 shown in FIG. 1 also can be located within the protection device 3, at this time, the modules constituting the high frequency and high voltage generator 5 shown in FIG. 1 located within the protection device 3 are electrically connected with the modules constituting the high frequency and high voltage generator 5 located between the housing body 1 and the protection device 3 or outside the housing body 1 via the circuit passage 311 or the wires or interfaces of the circuit passage 311 and the wire exiting passage 16.

Both the first end cap 31 and the second end cap 32 in the present embodiment are a double layered structure formed by the outer layer pate 331 and the inner layer plate 332 laminated to each other, and both the first end cap 31 and the second end cap 32 are opened with the circuit passage 311.

The circuit passage 311 opened on the first end cap 31 comprises the cathode positioning hole 313 opened on the inner layer plate 332 of the first end cap 31 and the wiring hole 340 opened on the outer layer plate 331 of the second end cap 32. The wire protection sleeve 314 outside the cathode 41 within the X-ray tube 4 is inserted into the cathode positioning hole 313. The wiring hole 340 includes the longitudinal hole 342 being coincident or parallel with the axial direction of protection device 3 and the transversal hole 341 in communication with the longitudinal hole 342 and the axial direction thereof being vertical to the axial direction of the longitudinal hole 342. The wire protection sleeve 315 of the cathode 41 within the X-ray tube 4 is inserted into the longitudinal hole 342, and the cathode 41 of the X-ray tube 4 is two conducting wires leading out of the transversal hole 341 from the wire protection sleeve 315.

The circuit passage 311 opened on the second end cap 32 includes anode positioning holes 316 provided on the inner layer plate 332 and the outer layer plate 331 of the second end cap 32, and the electric conducting bolt 317 in turn passes through the anode positioning holes 316 provided on the outer layer plate 331 and the inner layer plate 332 of the second end cap 32, and the external threading portion provided on the electric conducting bolt 317 is engaged with the anode screw hole provided on the anode 42. The electric conducting bolt 317 is opened with a positioning screw hole thereon at the portion away from the anode 42, and the positioning screw hole is engaged with the external threading portion provided on the electric conducting screw 318, and the conducting wire for electrically connecting with the anode of the high frequency and high voltage generator 5 is held between the head portion of the electric conducting screw 318 and the electric conducting bolt 317.

An annular spacer is collaredly provided between the electric conducting screw 318 and the electric conducting bolt 317, and the conducting wire electrically connected with the anode of the high frequency and high voltage generator 5 is held between the spacer and the head portion of the electric conducting screw 318.

Figure 12:
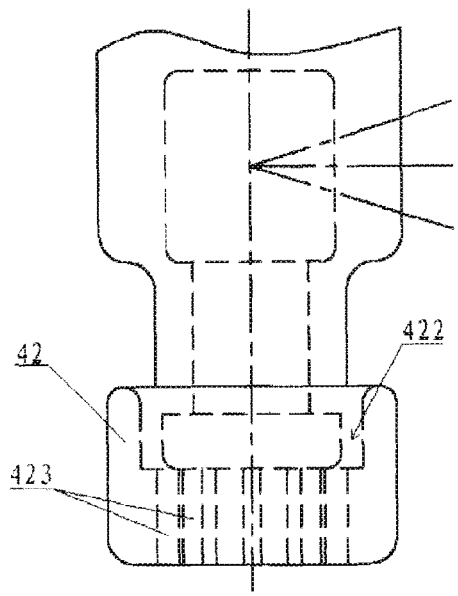
FIG. 12 is a perspective view of the anode portion of the X-ray tube within the radiation device installation housing according to the embodiment of the present invention.
Figure 13:
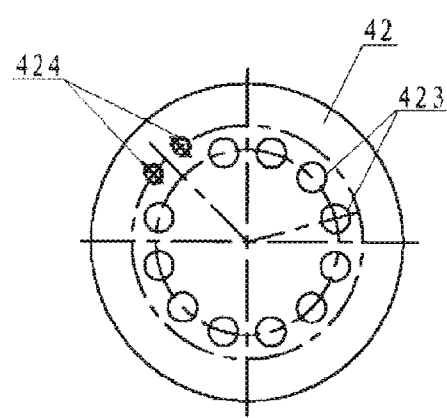
FIG. 13 is a bottom view of the anode portion of the X-ray tube shown in FIG. 12.

At least one of anode limit hole 320 is provided on the inner layer plate 332 as shown in FIG. 6 of the second end cap 32 in the present embodiment, a limit screw hole 424 is provided on the anode 42 shown in FIGS. 12 and 13, and the limit screw hole 424 is engaged with the external threading portion opened on the positioning bolt 421, one end on the positioning bolt 421 away from the limit screw hole 424 is inserted into the anode limit hole 320.

The number of the positioning bolts 421 and the anode limit holes 320 can be consistent and is two. Of course, the number of the positioning bolts 421 and the anode limit holes 320 can be one or more than three.

The fluid passage 312 is opened on both the first end cap 31 and the second end cap 32 in the present embodiment. Both the first end cap 31 and the second end cap 32 are the double layer structure formed by the outer layer plate 331 and the inner layer plate 332 laminated to each other. The liquid flow cavity 333 is presented between the outer layer plate 331 and the inner layer plate 332. The flow guiding hole 335 in communication with the liquid flow cavity 333 is opened on the inner layer plate 332, and the flow guiding hole 334 in communication with the liquid flow cavity 333 is opened on the outer layer plate 331. The fluid passage 312 is constituted by the flow guiding hole 334, the flow guiding hole 335 and the liquid flow cavity 333.

As shown in FIG. 12, the anode 42 is shaped in a cover form and is provided on the glass cover of the X-ray tube 4 away from the cathode 41. A liquid flow space 422 is disposed between the anode 42 and circumferential outer surface of the glass cover of the X-ray tube 4, and the liquid through hole 423 in communication with the liquid flow space 422 is opened on the anode 42. In the present embodiment, the axial direction of the liquid through hoe 423 is preferably parallel to the axial direction of the X-ray tube 4. The insulating liquid located outside the protection device 3 is flown into or out from the protection device 3 though the liquid passage 312 on the second end cap 32, the liquid through hole 423 and the liquid flow space 422.

In order to effectively position the anode 42, one or two or more circumferential screw holes 420 are provided on the circumferential outer surface of the anode 42, the anode 42 is circumferentially fixed within the protection device 3 through the screws passing through the cylindrical body 30 and inserted into the circumferential screw holes 420.

In order to simplify FIG. 12, the limit screws 424 and the circumferential holes 420 used to position the anode 42 shown in FIG. 12 are not shown in FIG. 13. The above configuration has advantages in easy and convenient installation.

The transversal hole 341 and the longitudinal hole 342 form the wiring hole 340 shaped in right angle folding line, such configuration can ensure that while the conducting wires are lead from the wiring hole 340, the X-ray emitted from the X-ray tube 4 is not able to pass through the wiring hole 340. Of course, the wiring hole 340 is also the angling hole or the through hole with other bending shapes (such as shaped in the acute angle or the obtuse angle folding line).

In the present embodiment, as shown in FIG. 5, the liquid outlet of the protection device 3 is located on the fluid passage 312 on the first end cap 31, and the liquid inlet of the protection device 3 is located on the fluid passage 312 on the second end cap 32.

Since the heat dissipated from the X-ray tube 4 is mainly from the anode 42 thereof, when the liquid inlet of the protection device 3 is located on the second end cap 32, the liquid inlet is closer to the anode 42 of the X-ray tube 4, and the insulating liquid with lower temperature is brought into contact with the anode 42 of the X-ray tube 4 firstly and carried away the heat on the anode 42 of the X-ray tube 4, which avoids the anode target of the X-ray tube 4 from damage due to the overheat. The target is positioned at the place where the X-ray (shown as the centerline) is emitted from the right side within the glass cover shown in FIG. 12.

In the present embodiment, the modules constituting the high frequency and high voltage generator 5 shown in FIG. 1 comprises the rectifier voltage-regulating module I 51, the high frequency inverter 52, the high voltage transformer 53 and the double voltage rectifier module 54 which are in turn electrically connected, wherein the rectifier voltage-regulating module I 51 is electrically connected with the housing external power supply 8 and is used to get the electric energy required for maintaining the DC high voltage applied on the cathode 41 and the anode 42 of the X-ray tube 4 from the housing external power supply 8. The double voltage rectifier module 54 is respectively electrically connected with the cathode 41 and the anode 42 of the X-ray tube 4.

The high voltage transformer 53 and the double voltage rectifier module 54 of the modules constituting the high frequency and high voltage generator 5 are fixedly arranged between the housing body 1 and the protection device 3 (shown in FIG. 2). The high voltage transformer 54 shown in FIG. 2 is fixedly arranged on the collimator 2, of course, it also can be fixedly arranged on the PCB plate, the first housing cover 14 or the second housing cover 15. The double voltage rectifier module 54 is fixedly arranged on the circuit board.

At least one end (the end at higher level shown in FIG. 3) of both ends of the circuit board is abutted against the limit lug 145 fixedly arranged on the first housing cover 14 or the limit lug 145 on the second housing cover 15 (in FIG. 3, abutted against the limit lug 145 on the first housing cover 14), and the circuit board is fixed onto the limit lug 145 by a fastener (preferable made of nylon materials).

Of course, in the present embodiment, the connection manners between the circuit board on which the double voltage rectifier module 54 is fixedly arranged and the housing 1 is not limited, for example, at least one end of both ends of the circuit board also can be embedded into the groove on the first housing cover 14 or the second housing cover 15, and the central region of the circuit board is fixed onto the housing main body 13 through a fastener. The fastener is used to prevent the circuit board from vibrating or deforming, so as to avoid the double voltage rectifier module 54 from damage due to the vibration.

The above fixing and assembling manners for the modules constituting the high frequency and high voltage generator 5 shown in FIG. 1 can allow a compact structure and sufficiently utilize the space within the housing body 1.

Of course, the double voltage-regulating module 54 also can be fixedly arranged on the surface of the protection device 3. The high voltage transformer 53 also can be fixedly arranged on one side of the first housing cover 14 or the second housing cover 15 brought in contact with the insulating liquid.

In the present embodiment, the rectifier voltage-regulating module I 51 is fixedly provided outside the housing body 1, and comprises a full bridge rectifier module and a BUCK chopping voltage-regulating module. The full bridge rectifier module converts the AC power supplied by the housing external power supply 8 into the DC power. The BUCK chopping voltage-regulating module is used to convert the constant DC voltage into the variable DC voltage, that is, after DC/DC conversion, the DC voltage is inputted into the high frequency inverter 52.

The high frequency inverter 52 is also fixedly provided outside the housing body 1, and inverts the low voltage DC power into the high frequency low voltage AC power by using a full-bridge series-parallel resonant high-frequency inversion circuit.

The high voltage transformer 53 is used to allow the voltage outputted from the high frequency inverter 52 to input into the double voltage rectifier module 54 after stepping-up. The double voltage rectifier module 54 has multi-stages (more than two-stages double voltage rectifier circuit, the double voltage rectifier module 54 achieves functions of stepping-up and rectifying (AC to DC)).

Since both the high voltage transformer 53 and the double voltage rectifier module 54 are usually applied with the high voltage over thousand volts, when the high voltage transformer 53 and the double voltage rectifier module 54 are provided between the housing body 1 and the protection device 3 and are immersed in the insulating liquid, the insulating liquid not only can prevent the high voltage transformer 53 and the double voltage rectifier module 54 from bombarding due to the high voltage, but also the heat generated thereon can be carried away by the flown insulating liquid.

As shown in FIG. 1 and FIG. 3, the X-ray generator in the present embodiment also includes a monitoring system, which comprises the signal sampling module 91, the sampled signal processing module 92, the logic determination control module 93 and the secondary power supply module 94 for supplying the power to the logic determination control module 93 as shown in FIG. 1.

The signal sampling module 91 is located between the housing body 1 and the protection device 3. The installation space between the housing body 1 and the protection device 3 is big, so that the signal sampling module 91 is adapted to be installed therein. Moreover, the signal sampling module 91 also can be installed within the protection device 3.

The signal sampling module 91 is used to detect the electric signals on the cathode 41 and the anode 42 of the X-ray tube 4, the temperature of the insulating liquid and the flow rate of the insulating liquid flowing into the housing body 1, and to send the detected electric signals to the sampled signal processing module 92.

The sampled signal processing module 92 is electrically connected with the signal sampling module 91 and the logic determination control module 93, respectively. The sampled signal processing module 92 is used to perform filtering or other processing for the electric signals received from the signal sampling module 91, so as to eliminate the related interference signal, and after the analog-digital electric signals are converted into the form of the digital values (e.g. binary), then send the detection result to the logic determination control module 93.

The logic determination control module 93 in the present embodiment is interacted with the external data via the serial communication interface 95 shown in FIG. 1. Of course, the interaction can be achieved by employing other communication interfaces or conducting wires or even in the form of sending or receiving the wireless signals.

The logic determination control module 93 will not output the detection results, rather than self-call the pre-stored control commands in accordance with the detection results according to the rule of which the preset detection results correspond to the control commands, and control all or a part of the output voltage and/or current from the high frequency and high voltage generator 5, the output voltage and/or current from the filament power supply module 6 and the power consumption of the oil pump 721 based on the control commands. Such implementation features high automatic processing and control.

As shown in FIG. 1, the signal sampling module 91 includes kV/mA sampling circuit 911, the temperature sensor 912, the flow rate sensor 913.

The kV/mA sampling circuit 911 is used to detect the voltage and/or current on the high voltage circuit constituted by the cathode 41 and the anode 42 of the X-ray tube 4. The kV/mA sampling circuit 911 mainly includes a kV high voltage divisor, a mA sampling resistance, a flashover mutual inductor. The kV/mA sampling circuit 911 is integrated with the double voltage rectifier module 54 shown in FIG. 2. Of course, the kV/mA sampling circuit 911 and the double voltage rectifier module 54 also can be two separate portions and the kV/mA sampling circuit 911 is only electrically connected with the double voltage rectifier module 54.

The temperature sensor 912 is used to detect the temperature of the insulating liquid.

The flow rate sensor 913 is used to detect the flow rate of the insulating liquid in the fluid passage 312 shown in FIG. 5.

In the present embodiment, the electric signals sent from the temperature sensor 912 and the flow rate sensor 913 are in the switching value (binary) form, at this time, the analog-digital conversion is not required, thus, the work load of the sampled signal processing module 92 is reduced. Of course, the electric signals sent from the temperature sensor 912 and the flow rate sensor 913 also can be in the form of analog value.

The type of the fault signals collected by the signal sampling module 91 includes the flow rate fault signal, the temperature fault signal and the flashover fault signal.

If the flow rate is not in the range of the predetermined value, the electric signal fed back to the sampled signal processing module 92 to reflect the over limit flow rate are treated as the flow rate fault signal. In a similar way, if the temperature exceeds the predetermined value, the electric signal fed back to the sampled signal processing module 92 to reflect overheat is treated as the temperature fault signal. If the collected voltage value and/or the current value is abnormal, it can be determined whether the flashover fault exists according to the abnormal voltage value and/or the current value, so that the abnormal voltage value and/or current value can be treated as the flashover fault signal.

As shown in FIG. 3, the flow rate sensor 913 is fixedly arranged on the liquid entering pipe 17 of the housing body 1, all of the insulating liquid flowing into the housing body 1 from the radiator 722 are passed through the liquid entering pipe 17, so that the flow rate of the insulating liquid flowing into the housing body 1 can be accurately detected on the liquid entering pipe 17. Furthermore, the flow rate sensor 913 also can be fixedly arranged on the liquid exiting opening 110 of the housing body 1, at this time, the flow rate of the insulating liquid flowing out of the housing 1 can be detected, since the amount of the insulating liquid within the housing body 1 is constant, the flow rate of the whole insulating liquid flowing out of the housing body 1 can be detected, and the flow rate of the insulating liquid flowing into the housing body 1 can be deduced.

As shown in FIG. 3, a temperature sensor 912 is fixedly arranged in the vicinity of the wire exiting passage 16. At this time, the temperature sensor 912 is easily led out from the wire exiting passage 16.

In the present embodiment, the filament power supply module 6 shown in FIG. 1 includes a rectifier voltage-adjusting module II 61 electrically connected with the logic determination control module 93, a filament inverter 62 and a filament transformer 63 respectively electrically connected with the filament inverter 62 and the cathode 41 of the X-ray tube 4.

The filament inverter 62 has a half-bridge structure, and the filament transformer 63 is fixedly arranged at the position where the inner wall of the housing main body 13 shown in FIG. 2 is in proximity to the first housing cover 14. The filament transformer 63 is a step-down transformer, which is used to convert the voltage outputted from the filament inverter 62 into the high frequency pulse voltage required for the cathode 41 of the X-ray tube 4 and then output to the cathode 41 of the X-ray tube 4.

The interfaces passing through the wire exiting passage 16 on the housing body 1 as shown in FIG. 3 is aviation plugs achieving the liquid-gas sealing function between the internal and the external of the housing body 1, and the high voltage transformer 53 and the high frequency inverter 52, the signal sampling module 91 and the sampled signal processing module 92, as well as the filament inverter 62 and the filament transformer 63 are all electrically connected via the aviation plugs 161.

The voltages applied on the rectifier voltage-adjusting module I 51, the high frequency inverter 52 and the logic determination control module 93 are lower. In order to both save the volume of the housing body 1 and be in convenient in mounting, disassembling, electrically connecting and setting the parameters, in this embodiment, the rectifier voltage-adjusting module I 51, the high frequency inverter 52, the logic determination control module 93, the rectifier voltage-adjusting module II 61, the filament inverter 62 and the secondary power supply module 94 are all fixedly provided on the outer surface of the housing body 1; however, the rectifier voltage-adjusting module I 51, the high frequency inverter 52, the rectifier voltage-adjusting module II 61, the filament inverter 62 and the logic determination control module 93 also can be fixedly provided within the control box outside the housing body 1. The control box can be either fixedly provided on the outer surface of the housing body 1 or separately provided on other frame or cabinet, and the related electric signals led out from the control box can be electrically connected with the aviation plugs 161 shown in FIG. 3 through the conducting wire passing through the control box.

As shown in FIG. 3 and FIG. 10, the aviation plugs 161 have the advantages in good sealing effect, being easy to be installed and a stable electric signal transmission. The interface also can be the combination of the conducting wire and the sealing member such as the sealing ring.

Of course, the high transformer 53 and the high inverter 52, the signal sampling module 91 and the sampled signal processing module 92 as well as the filament inverter 62 and the filament transformer 63 are electrically connected partially through the aviation plugs 161 and partially through the cables or other interfaces.

Two or more screw holes 21 are opened on the collimator 2 shown in FIG. 2 of the present embodiment, and the installation holes being coaxial with the screw holes 21 are opened on the housing body 1. The housing body 1 (the housing main body 13 as shown in FIG. 5) is fixedly connected with the collimator 2 by the screws in turn passing through the installation holes and the screw holes 21.

The connection structure constituted by the screw holes 21 and the screws is easily to be assembled and disassembled. When the X-ray generator provided in this embodiment is installing, firstly, the oil pump 721, the filament transformer 63, the circuit board provided with the double voltage rectifier module 54 and aviation plugs 161 are integrally mounted on the first housing cover 14, and the X-ray tube 4 is installed between the first end cap 31 and the second end cap 32 of the protection device 3 and the relevant electrical connection is completed. Then, the whole unity is pushed into the housing body 1, and the protection device 3 (including the collimator 2) is fixed on the housing main body 13 shown in FIG. 5 by screws, and then the oil feeding pipe 17 and the oil exiting opening 110 are connected Finally, the first housing cover 14 and the second housing cover 15 are hermetically fixed on the housing main body 13.

Furthermore, the screws also can be replaced by other threading fasteners such as the screw bolt or the threaded bolt. As shown in FIG. 2, the number of the screw holes 21 can be one, one row or multi rows (more than two rows), and the specific number can be determined according to the actual requirements (for example, the size of the screws or the screw bolts employed on site).

As shown in FIG. 5 and FIG. 8, the radiation device installation housing in the present embodiment includes the housing body 1 as described above, and further comprises a flange 18 having a circular shape fixedly arranged on the inner wall of the housing body 1 and a compensation device fixedly or movably connected with the flange 18 in the liquid tight manner.

The liquid receiving cavity for receiving the insulating liquid is formed between one side of both sides of the compensation device and the inner wall of housing body 1 as well as the flange 18.

A compensation device moving space for allowing the compensation device to deform or move in the direction away from or close to the insulting liquid is formed between the inner wall of the housing 1 opposite to another side of both sides of the compensation device and the inner wall of the flange 18.

Since the flange 18 in the present invention is located on the inner wall of the housing body 1, the compensation device and the flange 18 are fixedly or movably connected in the liquid tight manner, when the housing body 1 includes the housing main body 13, the first housing cover 14 and the second housing cover 15 shown in FIG. 5, they can be then assembled into an integral housing body after the compensation device is separately mounted on the flange 18 on the second housing cover 15. Thereby, the assembling for the compensation device and the assembling for the housing body can be performed separately, and when doing so, it not only can save energy and be convenient for the installation, but also can avoid operation mistakes. Also, since the height of the flange 18 can be designed based on the requirements, the depth and the size of the compensation device moving space can be designed based on the requirements. The flange 18 does not only have the function for fixing the compensation device, in the meanwhile, the flange 18 also has guiding function for the deformation or movement directions of the compensation device, so that the deformation or movement directions of the compensation device will be more regular. In addition, since the inner radius of the flange 18 is smaller than the second housing cover 15, the area of the compensation device required in the present invention is smaller than the second housing cover 15, thereby, the material consumption of the compensation device is less. Moreover, the connection operation between the flange 18 and the compensation device is performed within the housing body 1, thus, the liquid tight effect is desirable.

In the present embodiment, the compensation device is an elastic drum membrane 19 shown in FIG. 5 or 8 fixedly connected with the port of the flange 18 away from the inner wall of the housing body 1 and covering on the port of the flange 18 away from the inner wall of the housing body 1, and the elastic drum membrane 19 is able to be deformed in the direction away from or close to the insulating liquid within the compensation device moving space.

When the insulating liquid is thermally expanded, the expanded insulating liquid will press the elastic drum membrane 19 to allow the elastic drum membrane 19 to be deformed toward the direction away from the insulating liquid, that is, close to the second housing cover 15, and press the insulating liquid; when the insulating liquid is thermally contracted, the volume of the insulating liquid is shrunk, and the elastic drum membrane 19 will be deformed toward the direction close to the insulating liquid, that is, away from the second housing cover 15 and press the insulating liquid, so as to compensate the thermal expansion and contraction of the insulating liquid in the manner of elastic deformation, such that the insulating liquid is assured to be filled everywhere within the housing body 1, and the pressure, which the electrical components within the housing body 1 have been undergone, from the insulating liquid is substantially constant, and the housing body 1 and the electrical components within the housing body 1 are not be crushed or damaged because of the pressure from the insulating liquid being too large, and at the same time, when the oil is injected into the housing body 1 in the vacuum oil injection manner, after the process of injecting the insulating liquid into the housing 1 is over, the elastic drum membrane 19 will press the insulating liquid by means of elastically deformation, which ensures the insulating liquid being filled all over the housing body 1 and then, ensures the oil amount within the housing body 1 to meet the requirements.

Furthermore, the compensation device also can be the piston (not shown) embedded into the flange 18 shown in FIG. 2. The piston can be slidingly moved within the compensation device moving space toward the direction away from or close to the insulating liquid. At this time, an escape prevention structure to block the piston from escaping out of the flange 18 is provided between the piston and the inner wall of the flange 18. The escape prevention structure also can be the projecting edge fixedly arranged on the inner wall of the flange 18 away from the insulating liquid, and the projecting edge and the inner wall of the housing body can be an integrated structure.

In the present embodiment, an air guiding hole 114 to be in communication with the outside air (outside of the housing body 1) and the compensation device moving space is arranged on the housing body 1 as shown in FIG. 5. While the elastic drum membrane 19 is deformed in the direction of being close to the second housing cover 15, the air hole 114 can press the air within the compensation device moving space and allow the air within the compensation device moving space to discharge through the air guiding hole 114. When the elastic drum membrane 19 is deformed toward the direction of being away from the second housing cover 15, the air outside of the housing body 1 is flown into the compensation device moving space, so it is ensured that the elastic drum membrane 19 is more easily deformed within the compensation device moving space. The opening size of the air guiding hole 114 can be arbitrarily set according to the requirements.

The arrangement of the compensation device moving space increases the space for the deformation of the elastic drum membrane 19. Of course, in order to achieve the function of the elastic drum membrane 19, other elastic structures or elastic members instead of above structures are also provided within the housing body 1, of course, they require the matched movement and protection designs. For example, an inflation bag in communicating with the air guiding hole 114 and having elasticity is fixedly arranged within the housing body 1, and the joint between the inflation bag and the air guiding hole 114 is the liquid tight connection to avoid the insulating liquid from permeating out of the housing body 1 at the joint between the inflation bag and the air guiding hole 114. The inflation bag is in communication with the atmosphere through the air guiding hole 114. The inflation bag adopts the same concept as the elastic drum membrane 19 to compensate for the thermal expansion and contraction of the insulating liquid by the way of elastic deformation. However, when the oil is injected into the housing body 1 by employing the external vacuum oil injection method, if the inflation bag does not have the protective measures, the inflation bag is always ensured to be filled with the desired amount of the air, to assure that the inflation bag is always able to apply a certain of elastic pressure to the insulating liquid; or at the same time, the inflation bag is vacuumed so as to prevent the inflation bag from breaking due to the expansion. Furthermore, the inflation bag mode also has sealing problem.

In this embodiment, a pressing plate 20 is provided at one side of the elastic drum membrane 19 shown in FIG. 5 away from the inner wall of the housing body 1. The edges of the pressing plate 20 press the sides of the elastic drum membrane 19 against onto the flange 18, and the edges of the pressing plate 20 are fixedly connected with the flange 18 by fasteners 201. A plurality of through holes 202 (more than two) as shown in FIG. 5 through which the insulating liquid can freely pass are opened at the central region of the pressing plate 20.

As shown in FIG. 8, in the present embodiment, at least one of projections 191 formed in an external protruding shape are provided at one side of the elastic drum membrane 19 in proximity to the flange 18 or the pressing plate 20, a recess formed in an internal concave shape is provided on the flange 18 or the pressing plate 20, and the projection 191 is inserted in the recess.

The fitting structure formed by the projections 191 and the recess is more reliable in sealing. The fitting between the projections 191 and the recess preferably is the interference fit.

The projections 191 in the present embodiment are shaped in annular and the central axis thereof is coincident with the central axis of the flange 18. In such configuration, the sealing between the whole flange 18 and the elastic drum membrane 19 is relatively reliable.

The effects of the pressing plate 20 are in that the elastic drum membrane 19 is securely fixed, and the damage of the elastic drum membrane 19 caused by the deformation thereof such that the elastic drum membrane 19 excessively extends out of the flange 18 is avoided, and in the meanwhile, a plurality of through holes 202 on the pressing plate 20 also can ensure that the insulating liquid is able to contact with the elastic drum membrane 19, so that the effect of the elastic drum membrane 19 can be played. The pressing plate 20 is designed such that the X-ray generator is adapted to use both oil injection methods in external and internal of the vacuum apparatus. Furthermore, the pressing plate 20 can be replaced by employing a filter screen or other fixing structure.

In the present embodiment, as shown in FIGS. 5 and 8, the central region of one side of the elastic drum membrane 19 close to the pressing plate 20 is formed in a corrugation shape. The corrugation elastic drum membrane 19 has better elasticity. Since the edge region of the elastic drum membrane 19 is relatively flat, the portion of the elastic drum membrane 19 having the corrugation shape is directly provided at the central portion of the flange 18, so two portions can be aligned and the installation of the elastic drum membrane 19 is relatively easy.

In the present embodiment, as shown in FIG. 5, the edges of the pressing plate 20 are fixedly connected with the flange 18 through the fasteners 201. The fasteners 201 are screws or other fasteners.

As shown in FIG. 5, in the present embodiment, the flange 18 and the second housing cover 15 are integrated structure. When the flange 18 is integrated with the second housing cover 15, it is easy to be produced in one-step, and comparing to the structure assembled by the independent parts, the connection strength between each parts is firmer. Furthermore, the flange 18 can be integrated with one of the first housing cover 14 or the housing main body 13, or the flange 18 can be separated with the first housing cover 14, the second housing cover 15 or the housing main body 13 and fixedly connected. The number of the flange 18 within the housing body 1 can be provided in one or more than two according to the amount of the thermal expansion and contraction of the insulating liquid.

In the present embodiment, as shown in FIGS. 5 and 10, a plurality of reinforced ribs 22 (more than two) for integrating with the housing main body 13 are disposed at the outer surface of the housing main body 13. Screw holes 21 are opened on the reinforced ribs 22, and the reinforced ribs 22 are symmetrically provided on the housing main body 13.

On one hand, the reinforced ribs 22 can enforce the strength of the housing main body 13, and on the other hand, the screw holes 21 on the reinforced ribs 21 can be detachably fixedly connected with the other apparatus or frames externally provided.

Furthermore, the reinforced ribs 22 also can be provided on the first housing cover 14 or the second housing cover 15, and the number of the reinforced rib 22 can be one.

As shown in FIGS. 2, 3 and 5, in the present embodiment, the flange 18 is shaped in circular, at this time, the outer profile of the cross section of the flange 18 is formed in a circular shape, and the pressing plate 20 is formed in a disk shape. The fasteners 201 are equiangularly distributed on the pressing plate 20, the elastic drum membrane 19 and the flange 18 in the circumferential direction.

In such configuration, pressures from the fasteners applied at everywhere of the pressing plate 20, the elastic drum membrane 19 and the flange 18 are more uniform, and the pressing plate 20, the elastic drum membrane 19 and the flange 18 are not easy to be damaged, and at the same time, the stability of the fixed connection among them is better.

Furthermore, the cross section of the flange 18 can be selected from one of elliptic, triangular, rectangular (including oblong, square) or polygonal (in addition to the triangular and the rectangular) shapes. When the cross section of the flange 18 is shaped in rectangular, the pressing plate 20 is a rectangular plate. The flange 18 and the pressing plate 20, the elastic drum membrane 19 and so on provided thereon also can be arranged on the protection device 3, for example, can be provided on one of the cylindrical body 30, the first end cap 31 or the second end cap 32, at this time, the protection device 3 can be treated as a radiation device installation housing per se, thus, it falls within the protection scope of the present invention.

In the present embodiment, the material for producing the elastic drum membrane 19 is nitrile-butadiene rubber. Furthermore, the elastic drum membrane 19 also can be made in other oil-proof elastic materials such as fluorine rubber material and so on.

It should be noted that above embodiments only are used to explain the technical solutions of the present invention and are not the limitation thereto. Although the present invention is described in detail by referring the preferable embodiment, those skills in the art may understand that the embodiments of the present invention can be modified or the partial technical features are replaced with equivalents without departing the spirits of the technical solution of the present invention, which should be fallen into the scope of the present invention.

The invention claimed is:

1. A radiation device installation housing, comprising:
a housing body, comprising:
a flange fixedly provided on an inner wall of the housing body and shaped in circular; and
a compensation device fixedly or movably connected with the flange in a liquid tight manner;
a liquid receiving cavity for receiving an insulating liquid is formed between one side of two opposite sides of said compensation device and said inner wall of the housing body as well as said flange; and
a compensation device moving space for allowing said compensation device to deform or move toward a direction away from or close to said insulating liquid is formed between another side of said two opposite sides of said compensation device opposed to said inner wall of the housing body and an inner wall of the flange.

2. The radiation device installation housing according to claim 1, wherein said compensation device is an elastic drum membrane which is able to fixedly connect with a port of said flange away from said inner wall of the housing body and cover on the port of said flange away from said inner wall of the housing body, said elastic drum membrane is able to deform within said compensation device moving space toward the direction away from or close to said insulating liquid;
or, said compensation device is a piston embedded in said flange, said piston is able to move within said compensation device moving space toward the direction away from or close to said insulating liquid, an escape protection structure used to prevent the piston from escaping from said flange is further provided between said piston and said inner wall of the flange.

3. The radiation device installation housing according to claim 2, wherein an outer profile of the cross section of said flange is shaped in one of circular, elliptic, triangular, rectangular, or polygonal in addition to the triangular and the rectangular;
and/or, air guiding holes respectively in communication with the external air and said compensation device moving space are opened on said housing body;
and/or, materials for producing said elastic drum membrane is nitrile-butadiene rubber or fluorine rubber;
and/or, said elastic drum membrane is fixedly on said flange through fasteners, or one side of said elastic drum membrane away from said inner wall of the housing body comprises a pressing plate, an edge of said elastic drum membrane is pressed against onto said flange by an edge of said pressing plate, and said edge of the pressing plate is fixedly connected with said flange through fasteners, a central region of said pressing plate is opened with one or two or more through holes through which the insulating liquid is freely passed;
and/or, a central region of one side of said elastic drum membrane closed to said pressing plate is formed in corrugation;
and/or, said pressing plate is formed in a disk shape, and said fasteners are equiangularly distributed on said pressing plate, said elastic drum membrane and said flange in a circumferential direction of said pressing plate;
and/or, said radiation device installation housing further comprises a housing main body, a first housing cover and a second housing cover, wherein:
said first housing cover and said second housing cover are respectively fixedly provided on two opposite ports of said housing main body, and said flange is fixedly provided on said second housing cover or said first housing cover;
said housing main body has an integrated structure, and the material for producing said first housing cover and said second housing cover is the same as the material of said housing main body.

4. The radiation device installation housing according to claim 3, further comprising:
at least one projection having external protruding shape fixedly provided at one side of said elastic drum membrane close to said flange or said pressing plate, a recess having concave shape is opened on said flange or said pressing plate, said at least one projection is embedded in said recess;
and/or, said housing main body is made in aluminum or aluminum-alloy material by employing stretching process or cutting process;
and/or, said flange is integrated with said second housing cover;
and/or, said housing main body comprises at least one reinforced rib disposed on an outer surface of said housing main body, and said at least one reinforced rib comprises screw holes;
and/or, the radiation device installation housing further comprises a sealing strip between said first housing cover and said housing main body and/or between said second housing cover and said housing main body, wherein:
the radiation device installation housing further comprises a stepping face or a groove on an end surface of said housing main body, said sealing strip is embedded in said stepping face or said groove and extends out of the end surface of said housing main body, surfaces of said first housing cover and/or said second housing cover close to said housing main body are pressed against onto a portion of said sealing strip extending out of the end surface of said housing main body; or, a stepping face or a groove is opened on edges of said first housing cover and/or said second housing cover, said sealing strip is embedded in said stepping face or said groove and extends out of the edges of said first housing cover and/or said second housing cover, the surfaces of said housing main body close to said first housing cover and/or said second housing cover are pressed against onto a portion of said sealing strip extending out of the edges of said first housing cover and/or said second housing cover;

and/or, said radiation device installation housing further comprises a collimator and one or more layers of the protection device(s) provided within said housing body, wherein:

said one or more layers of protection device(s) is made in a material having shielding function to the X-ray; said collimator is integrated with said one or more layers of protection device(s), or, said collimator and said one or more layers of protection device(s) are two separate components fixedly connected together; each layer of said one or more layers of protection device is provided with a ray exit, and said ray exit, said beam exiting hole and said beam exiting opening are coaxial.

5. The radiation device installation housing according to claim 4, wherein said at least one projection is formed in annular, and a central axis thereof is coincident with a central axis of the flange;

and/or, said one or more layers of protection device(s) is formed in cylindrical or prismatic shape, and said one or more layers of protection device(s) include a cylindrical body, a first end cap and a second end cap, wherein: said first end cap and said second end cap are respectively fixedly connected with two opposite ports of the cylindrical body; a fluid passage and/or a circuit passage are/is provided on one of said first end cap, said second end cap or said cylindrical body;

and/or, a layer of said one or more layers of is protection device(s) are provided in said housing body, a space for flowing the liquid and installing the components are provided between said one or more layers of protection device(s) and said housing body; or, the one or more layers of protection device(s) include a plurality layers of said protection devices provided in said housing body, an inner layer of the protection device of the plurality layers of the protection devices is located within an outer layer of the protection device thereof, and spaces for flowing the liquid and installing the components are provided between the inner layer of the protection device and outer layer of the protection device as well as between an outmost layer of the protection device and said housing body;

and/or, said protection device is made of insulating materials;

and/or, the radiation device installation housing further comprises a blocking window filled in said beam exiting opening and is made in a material which the X-ray can penetrate, and said blocking window is used to achieve the liquid-air sealing between the inside and outside of the housing body.

6. The radiation device installation housing according to claim 5, wherein said one or more layers of protection device(s) are made of lead oxides;

and/or, said fluid passage and/or said circuit passage is a through hole or an angling hole having a bend shape at least opened on one of said first end cap, said second end cap or said cylindrical body; or at least one of said first end cap, said second end cap or said cylindrical body is a double layered structure configured by an outer layer plate and an inner layer plate laminated to each other, wherein:

the radiation device installation housing further comprises a liquid flowing cavity between said outer layer plate and said inner layer plate, and flow guiding holes in communication with said liquid flowing cavity are opened on both said outer layer plate and said inner layer plate, said fluid passage is constituted by said flow guiding holes and said liquid flowing cavity, an orthographic projection of the flow guiding hole along the axial direction thereof on the outer layer plate is completely staggered from the flow guiding hole on the inner layer plate.

7. The radiation installation device housing according to claim 6, wherein said one or more layers of protection device(s) are made of lead tetroxide;

and/or, said fluid passage and said circuit passage are provided on both said first end cap and said second end cap;

and/or, the radiation device installation housing further comprises an internal thread pipe embedded in the cylindrical body, the internal thread pipe comprises internal threads within the internal thread pipe, a portion of a connection bolt opened with external threads is penetrated through said outer layer plate and engaged with the internal threads within the internal thread pipe, and fixedly connected with said cylindrical body and said first end cap as well as said second end cap together;

and/or, the radiation device installation housing further comprises a positioning boss fixedly arranged on the inner layer plate, said positioning boss is inserted into a positioning counterbore on the outer layer plate and tightly mated with said positioning counterbore;

and/or, the radiation device installation housing further comprises a stepping portion shaped as steps on an edge at an inner side of the cylindrical body, said stepping portion is abutted against an edge of said inner layer plate;

and/or, at least one anode limit holes are opened on the inner layer plate of said second end cap, a limit screw hole is opened on said anode, an external thread portion engaged with said limit screw hole is opened on a positioning bolt, one end on said positioning bolt away from said limit screw hole is inserted into said anode limit hole;

and/or, the radiation device installation housing further comprises a plurality of flow guiding holes are equiangularly distributed on said outer layer plate and/or inner layer plate on said first end cap and/or said second end cap in a circumferential direction of said cylindrical body, and the distance from each of said flow guiding holes to the central axis of said cylindrical body is equal;

and/or, the radiation device installation housing further comprises a wiring hole on the outer layer plate in the first end cap, the wiring hole includes a longitudinal hole being coincident or parallel to the axial direction of the cylindrical body and a transversal hole in communication with said longitudinal hole and an axial direction of said transversal hole being vertical to an axial direction of said longitudinal hole.

8. An X-ray generator, comprising:
a radiation device installation housing claimed in any one of claims 1 to 7;
an X-ray tube, a high frequency and high voltage generator, a filament power supply module and an oil cooling circulation system, wherein:
the x-ray tube comprises a cathode and an anode;
said X-ray tube is installed within said one or more layers of protection device(s), and the X-ray emitted from said X-ray tube in turn passes through a ray exit, a beam exiting hole and a beam exiting opening and radiates out of the housing body of the radiation device installation housing;
said high frequency and high voltage generator is electrically connected with the cathode and the anode of said X-ray tube;
said filament power supply module is electrically connected with the cathode of said X-ray tube;
said oil cooling circulation system includes a liquid filling tank comprising the radiation device installation housing, an insulating liquid filled in the liquid filling tank and a cooling device used for reducing the temperature of said insulating liquid, said cooling device includes an oil pump, a radiator and a cooling fan, wherein:
said radiator is located outside said liquid filling tank, and a liquid ingress of said radiator is in communication with a liquid exit of said liquid filling tank, a liquid egress of said radiator is in communication with a liquid entrance of said liquid filling tank;
said oil pump is used to provide power to the circulation flow between the insulating liquid within said liquid filling tank and the insulating liquid within said radiator;
said cooling fan is used to dissipate the heat on said radiator by ways of accelerating the air flowing around said radiator.

9. The X-ray generator according to claim 8, wherein a circuit passage is opened on said protection device, said high frequency and high voltage generator is electrically connected with the cathode and anode of said X-ray tube via conducting wires or interfaces passing through said circuit passage;
at least one part of modules constituting said high frequency and high voltage generator are located between said protection device and the housing body, and a housing external power supply or other part of modules constituting said high frequency and high voltage generator are located outside the housing body;
a wire exiting passage is opened on the housing body, the part of modules constituting said high frequency and high voltage generator located within said housing body are electrically connected with the other part of modules constituting said high frequency and high voltage generator located outside the housing body or said high frequency and high voltage is electrically connected with said housing external power supply through the conducting wires or interfaces passing through the wire exiting passage;
said one or more layers of protection device(s) include a cylindrical body, a first end cap and a second end cap, said first end cap and said second end cap are respectively fixedly connected with two ports of said cylindrical body;
a fluid passage and said circuit passage are opened on at least one of said first end cap, said second end cap or said cylindrical body.

10. The X-ray generator according to claim 9, wherein both said first end cap and said second end cap are a double layered structure configured by an outer layer plate and an inner layer plate laminated to each other, and said circuit passages is provided on both said first end cap and said second end cap, wherein:
said circuit passage opened on said first end cap includes a cathode positioning hole opened on the inner layer plate on said first end cap and a wiring hole opened on the outer layer plate on said second end cap, a wire protection sleeve outside the cathode within said X-ray tube is embedded within said cathode positioning hole, said wiring hole includes a longitudinal hole coincident with or parallel to an axial direction of said X-ray tube and a transversal hole in communication with said longitudinal hole and an axial direction of the transversal hole being vertical to an axial direction of said longitudinal hole, the cathode of said X-ray tube is extracted out of said wiring hole through two conducting wires from said wire protection sleeve;
said circuit passage opened on said second end cap includes anode positioning holes opened on said inner layer plate and said outer layer plate of the second end cap, an electric conducting bolt in turn passes through said anode positioning holes opened on said outer layer plate and said inner layer plate of said second end cap, and an external thread portion opened on said electric conducting bolt is engaged with an anode screw hole opened on said anode, a positioning screw hole is opened on a portion of said electric conducting bolt away from said anode, and the external thread portion opened on an electric conducting screw is engaged with said positioning screw hole, and the conducting wires respectively electrically connected with the anode of the high frequency and high voltage generator are held between a head portion of said electric conducting screw and said electric conducting bolt;
and/or, a fluid passage is opened on both said first end cap and said second end cap, both said first end cap and said second end cap are a double layered structure formed by an outer layer plate and an inner layer plate laminated to each other, a liquid flowing cavity is provided between said outer layer plate and said inner layer plate, and flow guiding holes in communication with said liquid flowing cavity are opened on both said outer layer plate and said inner layer plate, said fluid passage is formed by said flow guiding holes and said liquid flowing cavity;
said anode has a cover shape and covers at one end on a glass cover of said X-ray tube away from the cathode, a liquid flowing space is provided between the anode and a circumferential outer surface of the glass cover of the X-ray tube, liquid through holes respectively in communication with the liquid flowing space and said flow guiding holes on said inner layer plate on the second end cap are provided on the anode.

* * * * *